United States Patent
Li et al.

(10) Patent No.: US 11,213,528 B2
(45) Date of Patent: *Jan. 4, 2022

(54) SALTS OF THE JANUS KINASE INHIBITOR (R)-3-(4-(7H-PYRROLO[2,3-D]PYRIMIDIN-4-YL)-1H-PYRAZOL-1-YL)-3-CYCLOPENTYLPROPANENITRILE

(71) Applicants: Incyte Holdings Corporation, Wilmington, DE (US); Incyte Corporation, Wilmington, DE (US)

(72) Inventors: Hui-Yin Li, Hockessin, DE (US); James D. Rodgers, Landenberg, PA (US)

(73) Assignees: Incyte Holdings Corporation, Wilmington, DE (US); Incyte Corporation, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/806,244

(22) Filed: Mar. 2, 2020

(65) Prior Publication Data

US 2020/0197401 A1    Jun. 25, 2020

Related U.S. Application Data

(63) Continuation of application No. 16/003,210, filed on Jun. 8, 2018, now Pat. No. 10,610,530, which is a continuation of application No. 15/164,518, filed on May 25, 2016, now Pat. No. 10,016,429, which is a continuation of application No. 14/270,915, filed on May 6, 2014, now Pat. No. 9,376,439, which is a continuation of application No. 14/097,588, filed on Dec. 5, 2013, now Pat. No. 8,722,693, which is a continuation of application No. 12/137,892, filed on Jun. 12, 2008, now abandoned.

(60) Provisional application No. 60/943,705, filed on Jun. 13, 2007.

(51) Int. Cl.
| | |
|---|---|
| A61K 31/519 | (2006.01) |
| A61P 17/12 | (2006.01) |
| A61P 17/06 | (2006.01) |
| A61P 17/08 | (2006.01) |
| C07D 487/04 | (2006.01) |
| A61K 9/00 | (2006.01) |
| A61K 9/20 | (2006.01) |

(52) U.S. Cl.
CPC .......... *A61K 31/519* (2013.01); *A61K 9/0053* (2013.01); *A61K 9/20* (2013.01); *A61P 17/06* (2018.01); *A61P 17/08* (2018.01); *A61P 17/12* (2018.01); *C07D 487/04* (2013.01); *C07B 2200/07* (2013.01); *C07B 2200/13* (2013.01)

(58) Field of Classification Search
CPC ............. C07D 487/04; A61K 31/519
USPC ........................ 544/280; 514/265.1
See application file for complete search history.

(56) References Cited

U.S. PATENT DOCUMENTS

| | | |
|---|---|---|
| 2,985,589 A | 5/1961 | Broughton et al. |
| 3,832,460 A | 8/1974 | Kosti |
| 4,140,755 A | 2/1979 | Sheth |
| 4,402,832 A | 9/1983 | Gerhold |
| 4,498,991 A | 2/1985 | Oroskar |
| 4,512,984 A | 4/1985 | Seufert et al. |
| 4,548,990 A | 10/1985 | Mueller et al. |
| 4,814,477 A | 3/1989 | Wijnberg et al. |
| 5,306,713 A | 4/1994 | Suetsugu et al. |
| 5,378,700 A | 1/1995 | Sakuma et al. |
| 5,472,949 A | 12/1995 | Arasaki |
| 5,510,101 A | 4/1996 | Stroppolo |
| 5,521,184 A | 5/1996 | Zimmermann |
| 5,630,943 A | 5/1997 | Grill |
| 5,795,909 A | 8/1998 | Shashoua et al. |
| 5,856,326 A | 1/1999 | Anthony |
| 5,919,779 A | 7/1999 | Proudfoot et al. |
| 6,025,366 A | 2/2000 | Walsh et al. |
| 6,069,038 A | 5/2000 | Burns |
| 6,075,056 A | 6/2000 | Quigley, Jr. et al. |
| 6,136,198 A | 10/2000 | Adam et al. |
| 6,217,895 B1 | 4/2001 | Guo |
| 6,335,342 B1 | 1/2002 | Longo et al. |
| 6,375,839 B1 | 4/2002 | Adam et al. |
| 6,413,419 B1 | 7/2002 | Adam et al. |
| 6,486,322 B1 | 11/2002 | Longo et al. |
| 6,518,265 B1 | 2/2003 | Kato et al. |
| 6,548,078 B2 | 4/2003 | Guo |
| 6,569,443 B1 | 5/2003 | Dawson |
| 6,579,882 B2 | 6/2003 | Stewart et al. |
| 6,624,138 B1 | 9/2003 | Sung et al. |
| 6,635,762 B1 | 10/2003 | Blusnenkopf et al. |

(Continued)

FOREIGN PATENT DOCUMENTS

| | | |
|---|---|---|
| CN | 102026999 | 4/2011 |
| CN | 102985417 | 3/2013 |

(Continued)

OTHER PUBLICATIONS

Pardanani et al., "CSF3R T618I is a highly prevalent and specific mutation in chronic neutrophilic leukemia," Leukemia, 2013, 27:1870-1873.

(Continued)

*Primary Examiner* — Susanna Moore

(74) *Attorney, Agent, or Firm* — Brian C. Trinque; Lathrop GPM LLP

(57) ABSTRACT

The present invention provides salt forms of (R)-3-(4-(7H-pyrrolo[2,3-d]pyrimidin-4-yl)-1H-pyrazol-1-yl)-3-cyclopentylpropanenitrile that are useful in the modulation of Janus kinase activity and are useful in the treatment of diseases related to activity of Janus kinases including, for example, immune-related diseases, skin disorders, myeloid proliferative disorders, cancer, and other diseases.

16 Claims, No Drawings

(56) References Cited

U.S. PATENT DOCUMENTS

| | | |
|---|---|---|
| 6,712,973 B2 | 3/2004 | Adam et al. |
| 6,713,089 B1 | 3/2004 | Bertelsen et al. |
| 6,852,727 B2 | 2/2005 | Goulet et al. |
| 6,953,776 B2 | 10/2005 | Di Napoli |
| 7,005,436 B2 | 2/2006 | Lloyd et al. |
| 7,167,750 B2 | 1/2007 | Knudson et al. |
| 7,265,108 B2 | 9/2007 | Ozaki |
| 7,335,667 B2 | 2/2008 | Rodgers et al. |
| 7,358,225 B2 | 4/2008 | Nakamura |
| 7,517,870 B2 | 4/2009 | Auricchio |
| 7,598,257 B2 | 10/2009 | Rodgers et al. |
| 7,683,171 B2 | 3/2010 | Pitts et al. |
| 7,745,437 B2 | 6/2010 | Ren et al. |
| 7,750,007 B2 | 7/2010 | Bearss et al. |
| 7,834,022 B2 | 11/2010 | Rodgers et al. |
| 8,053,433 B2 | 11/2011 | Rodgers et al. |
| 8,158,616 B2 | 4/2012 | Rodgers et al. |
| 8,309,718 B2 | 11/2012 | Li et al. |
| 8,410,265 B2 | 4/2013 | Zhou et al. |
| 8,415,362 B2 | 4/2013 | Rodgers et al. |
| 8,420,629 B2 | 4/2013 | Rodgers et al. |
| 8,440,679 B2 | 5/2013 | McAllister |
| 8,445,488 B2 | 5/2013 | Rodgers et al. |
| 8,486,902 B2 | 7/2013 | Rodgers et al. |
| 8,513,270 B2 | 8/2013 | Arvanitis et al. |
| 8,530,485 B2 | 9/2013 | Rodgers et al. |
| 8,541,425 B2 | 9/2013 | Rodgers et al. |
| 8,563,541 B2 | 10/2013 | Arvanitis et al. |
| 8,604,043 B2 | 12/2013 | Li et al. |
| 8,637,529 B2 | 1/2014 | Woller |
| 8,691,807 B2 | 4/2014 | Yao et al. |
| 8,716,303 B2 | 5/2014 | Rodgers et al. |
| 8,722,693 B2 | 5/2014 | Rodgers et al. |
| 8,741,895 B2 | 6/2014 | Rodgers et al. |
| 8,748,401 B2 | 6/2014 | Rodgers et al. |
| 8,765,734 B2 | 7/2014 | Huang et al. |
| 8,822,481 B1 | 9/2014 | Rodgers et al. |
| 8,829,013 B1 | 9/2014 | Rodgers et al. |
| 8,835,423 B2 | 9/2014 | Arvanitis et al. |
| 8,841,318 B2 | 9/2014 | Arvanitis et al. |
| 8,883,806 B2 | 11/2014 | Zhou et al. |
| 8,889,697 B2 | 11/2014 | Rodgers et al. |
| 8,933,085 B2 | 1/2015 | Rodgers et al. |
| 8,933,086 B2 | 1/2015 | Rodgers et al. |
| 8,946,245 B2 | 2/2015 | Rodgers et al. |
| 8,987,442 B2 | 3/2015 | Tung et al. |
| 8,987,443 B2 | 3/2015 | Liu |
| 8,993,582 B2 | 3/2015 | Zhou et al. |
| 9,000,161 B2 | 4/2015 | Zhou et al. |
| 9,023,840 B2 | 5/2015 | Yao et al. |
| 9,034,884 B2 | 5/2015 | Rodgers et al. |
| 9,079,912 B2 | 7/2015 | Rodgers et al. |
| 9,090,611 B2 | 7/2015 | Rodgers et al. |
| 9,181,271 B2 | 11/2015 | Li et al. |
| 9,206,187 B2 | 12/2015 | Rodgers et al. |
| 9,216,984 B2 | 12/2015 | Zhou et al. |
| 9,221,845 B2 | 12/2015 | Cao |
| 9,249,145 B2 | 2/2016 | Rodgers et al. |
| 9,299,506 B2 | 3/2016 | Li et al. |
| 9,334,274 B2 | 5/2016 | Rodgers et al. |
| 9,358,229 B2 | 6/2016 | Vannucchi et al. |
| 9,359,358 B2 | 6/2016 | Rodgers et al. |
| 9,376,439 B2 | 6/2016 | Rodgers et al. |
| 9,464,088 B2 | 10/2016 | Huang Taisheng |
| 9,487,521 B2 | 11/2016 | Zhou et al. |
| 9,498,467 B2 | 11/2016 | Leopaid et al. |
| 9,611,269 B2 | 4/2017 | Yao et al. |
| 9,623,029 B2 | 4/2017 | Li et al. |
| 9,655,854 B2 | 5/2017 | Yeleswaram et al. |
| 9,974,790 B2 | 5/2018 | Rodgers et al. |
| 9,999,619 B2 | 6/2018 | Huang et al. |
| 2002/0111353 A1 | 8/2002 | Lededoer et al. |
| 2003/0064969 A1 | 4/2003 | Bhagwat et al. |
| 2003/0100756 A1 | 5/2003 | Adams et al. |
| 2003/0144309 A1 | 7/2003 | Choon-Moon |
| 2003/0165576 A1 | 9/2003 | Fujii et al. |
| 2004/0009222 A1 | 1/2004 | Chou et al. |
| 2004/0009983 A1 | 1/2004 | Cox et al. |
| 2004/0029857 A1 | 2/2004 | Hale et al. |
| 2004/0077654 A1 | 4/2004 | Bouillot |
| 2004/0198737 A1 | 10/2004 | Cox et al. |
| 2004/0204404 A1 | 10/2004 | Zelle |
| 2004/0214928 A1 | 10/2004 | Aronov |
| 2004/0235862 A1 | 11/2004 | Burns |
| 2005/0014966 A1 | 1/2005 | Tabe |
| 2005/0054568 A1 | 3/2005 | Ling |
| 2005/0153989 A1 | 7/2005 | Grotzfed et al. |
| 2006/0004010 A1 | 1/2006 | Habashita et al. |
| 2006/0020011 A1 | 1/2006 | Wu et al. |
| 2006/0079511 A1 | 4/2006 | Liu et al. |
| 2006/0106020 A1 | 5/2006 | Rodgers et al. |
| 2006/0128803 A1 | 6/2006 | Klimko |
| 2006/0135537 A1 | 6/2006 | Knegtel et al. |
| 2006/0136027 A1 | 6/2006 | Furet et al. |
| 2006/0178393 A1 | 8/2006 | Pitts |
| 2006/0183761 A1 | 8/2006 | Ledeboer et al. |
| 2006/0183906 A1 | 8/2006 | Rodgers et al. |
| 2006/0223864 A1 | 10/2006 | Biju |
| 2006/0293311 A1 | 12/2006 | Li et al. |
| 2007/0135461 A1 | 6/2007 | Rodgers et al. |
| 2007/0135466 A1 | 6/2007 | Ledeboer et al. |
| 2007/0149506 A1 | 6/2007 | Arvanitis et al. |
| 2007/0149561 A1 | 6/2007 | Dhanak et al. |
| 2007/0191364 A1 | 8/2007 | Braun et al. |
| 2007/0191405 A1 | 8/2007 | Noronha |
| 2007/0208053 A1 | 9/2007 | Arnold et al. |
| 2007/0225286 A1 | 9/2007 | Ren et al. |
| 2007/0259904 A1 | 11/2007 | Noronha |
| 2008/0021026 A1 | 1/2008 | Borchardt et al. |
| 2008/0085898 A1 | 4/2008 | Lu |
| 2008/0096852 A1 | 4/2008 | Yanni |
| 2008/0119496 A1 | 5/2008 | Ohlmeyer |
| 2008/0161346 A1 | 7/2008 | Cheng |
| 2008/0188500 A1 | 8/2008 | Arvanitis et al. |
| 2008/0194468 A1 | 8/2008 | Bodor |
| 2008/0207570 A1 | 8/2008 | Segura-Orsoni |
| 2008/0207584 A1 | 8/2008 | Habashita et al. |
| 2008/0280876 A1 | 11/2008 | Hobson et al. |
| 2008/0312258 A1 | 12/2008 | Rodgers et al. |
| 2008/0312259 A1 | 12/2008 | Rodgers et al. |
| 2009/0018156 A1 | 1/2009 | Tang et al. |
| 2009/0076070 A1 | 3/2009 | Harada et al. |
| 2009/0088445 A1 | 4/2009 | Ledeboer et al. |
| 2009/0131403 A1 | 5/2009 | Kusuda |
| 2009/0181959 A1 | 7/2009 | Rodgers et al. |
| 2009/0197869 A1 | 8/2009 | Arvanitis et al. |
| 2009/0203637 A1 | 8/2009 | Hocek et al. |
| 2009/0215766 A1 | 8/2009 | Rodgers et al. |
| 2009/0221608 A1 | 9/2009 | Cui et al. |
| 2009/0233903 A1 | 9/2009 | Rodgers et al. |
| 2009/0318405 A1 | 12/2009 | Li et al. |
| 2010/0022522 A1 | 1/2010 | Rodgers et al. |
| 2010/0069381 A1 | 3/2010 | Itoh et al. |
| 2010/0113416 A1 | 5/2010 | Friedman et al. |
| 2010/0190981 A1 | 7/2010 | Zhou et al. |
| 2010/0210627 A1 | 8/2010 | Mao et al. |
| 2010/0298334 A1 | 11/2010 | Rodgers et al. |
| 2010/0298355 A1 | 11/2010 | Li et al. |
| 2011/0059951 A1 | 3/2011 | Rodgers et al. |
| 2011/0082159 A1 | 4/2011 | Rodgers et al. |
| 2011/0086810 A1 | 4/2011 | Rodgers et al. |
| 2011/0086835 A1 | 4/2011 | Rodgers et al. |
| 2011/0201593 A1 | 8/2011 | Babu et al. |
| 2011/0207754 A1 | 8/2011 | Li et al. |
| 2011/0223210 A1 | 9/2011 | Rodgers et al. |
| 2011/0224157 A1 | 9/2011 | Rodgers et al. |
| 2011/0224190 A1 | 9/2011 | Huang et al. |
| 2011/0288107 A1 | 11/2011 | Parikh et al. |
| 2012/0014989 A1 | 1/2012 | Rodgers et al. |
| 2012/0077798 A1 | 3/2012 | Rodgers et al. |
| 2012/0149681 A1 | 6/2012 | Rodgers et al. |
| 2012/0149682 A1 | 6/2012 | Rodgers et al. |
| 2012/0214825 A1 | 8/2012 | Vannucchi et al. |
| 2012/0225057 A1 | 9/2012 | Fynn |

(56) References Cited

U.S. PATENT DOCUMENTS

| | | |
|---|---|---|
| 2012/0252779 A1 | 10/2012 | Ramsden |
| 2012/0301464 A1 | 11/2012 | Friedman et al. |
| 2012/0329782 A1 | 12/2012 | Arvanitis et al. |
| 2013/0018034 A1 | 1/2013 | Yao et al. |
| 2013/0040973 A1 | 2/2013 | Vannuchi et al. |
| 2013/0045963 A1 | 2/2013 | Rodgers et al. |
| 2013/0060026 A1 | 3/2013 | Zhou et al. |
| 2013/0137681 A1 | 5/2013 | Rodgers et al. |
| 2013/0225556 A1 | 8/2013 | Rodgers et al. |
| 2013/0253190 A1 | 9/2013 | Zhou et al. |
| 2013/0253191 A1 | 9/2013 | Zhou et al. |
| 2013/0253193 A1 | 9/2013 | Zhou et al. |
| 2013/0274527 A1 | 10/2013 | Arvanitis et al. |
| 2013/0296299 A1 | 11/2013 | Rodgers et al. |
| 2014/0004516 A1 | 1/2014 | Sattler et al. |
| 2014/0018374 A1 | 1/2014 | Rodgers et al. |
| 2014/0031344 A1 | 1/2014 | Arvanitis et al. |
| 2014/0095166 A1 | 1/2014 | Rodgers et al. |
| 2014/0095210 A1 | 1/2014 | Rodgers et al. |
| 2014/0073657 A1 | 3/2014 | Li et al. |
| 2014/0094477 A1 | 4/2014 | Rodgers et al. |
| 2014/0121198 A1 | 5/2014 | Li et al. |
| 2014/0135350 A1 | 5/2014 | Ni et al. |
| 2014/0171409 A1 | 6/2014 | Yao et al. |
| 2014/0221379 A1 | 8/2014 | Rodgers et al. |
| 2014/0228346 A1 | 8/2014 | Rodgers et al. |
| 2014/0243360 A1 | 8/2014 | Rodgers et al. |
| 2014/0256941 A1 | 9/2014 | Liu et al. |
| 2014/0275031 A1 | 9/2014 | Huang et al. |
| 2014/0343030 A1 | 11/2014 | Li et al. |
| 2014/0378400 A1 | 12/2014 | Rodgers et al. |
| 2015/0065447 A1 | 3/2015 | Sandor |
| 2015/0065484 A1 | 3/2015 | Yeleswaram et al. |
| 2015/0087632 A1 | 3/2015 | Rodgers et al. |
| 2015/0087662 A1 | 3/2015 | Li et al. |
| 2015/0152117 A1 | 6/2015 | Gibbons et al. |
| 2015/0164900 A1 | 6/2015 | Rodgers et al. |
| 2015/0183805 A1 | 7/2015 | Liu et al. |
| 2015/0225411 A1 | 8/2015 | Yao et al. |
| 2015/0225412 A1 | 8/2015 | Brameld et al. |
| 2015/0238492 A1 | 8/2015 | Rodgers et al. |
| 2015/0246046 A1 | 9/2015 | Vaddi |
| 2015/0250790 A1 | 9/2015 | Parikh et al. |
| 2015/0315185 A1 | 11/2015 | Rodgers et al. |
| 2015/0342952 A1 | 12/2015 | Leopold |
| 2015/0344497 A1 | 12/2015 | Zhou et al. |
| 2016/0000795 A1 | 1/2016 | Scherle |
| 2016/0015695 A1 | 1/2016 | Li et al. |
| 2016/0024109 A1 | 1/2016 | Li |
| 2016/0067253 A1 | 3/2016 | Li et al. |
| 2016/0272648 A1 | 9/2016 | Rodgers et al. |
| 2016/0346286 A1 | 12/2016 | Rodgers et al. |
| 2016/0347734 A1 | 12/2016 | Liu et al. |
| 2017/0015674 A1 | 1/2017 | Zhou et al. |
| 2017/0071947 A1 | 3/2017 | Rodgers et al. |
| 2017/0087158 A1 | 3/2017 | Friedman et al. |
| 2017/0246157 A1 | 8/2017 | Huang et al. |
| 2017/0253598 A1 | 9/2017 | Yao et al. |
| 2017/0319487 A1 | 11/2017 | Yeleswaram et al. |

FOREIGN PATENT DOCUMENTS

| | | |
|---|---|---|
| DE | 30 36 390 A1 | 5/1982 |
| EP | 0223420 | 5/1987 |
| EP | 0727217 | 8/1996 |
| EP | 0795556 | 9/1997 |
| EP | 2343298 A1 | 7/2011 |
| JP | H07-010876 A | 1/1995 |
| JP | 2003-155285 A | 5/2003 |
| JP | 2006-502183 | 1/2006 |
| JP | 2006-518341 | 8/2006 |
| JP | 2008-508241 | 3/2008 |
| JP | 2008-545660 | 12/2008 |
| JP | 2009-504619 | 2/2009 |
| JP | 2010-529209 | 8/2010 |
| WO | 1996/030343 A1 | 10/1996 |
| WO | 1997/002262 A1 | 1/1997 |
| WO | 1997/002266 A1 | 1/1997 |
| WO | 1997/036587 A1 | 10/1997 |
| WO | 1997/038664 A1 | 10/1997 |
| WO | 1997/045412 A1 | 12/1997 |
| WO | 1998/044797 A1 | 10/1998 |
| WO | 1998/051391 A1 | 11/1998 |
| WO | 1999/000654 A2 | 1/1999 |
| WO | 1999/062908 A1 | 12/1999 |
| WO | 1999/065908 A1 | 12/1999 |
| WO | 1999/065909 A1 | 12/1999 |
| WO | 2000/009495 A1 | 2/2000 |
| WO | 2000/051614 A1 | 9/2000 |
| WO | 2000/053595 A1 | 9/2000 |
| WO | 2000/063168 A1 | 10/2000 |
| WO | 2001/014402 A1 | 3/2001 |
| WO | 01/027104 | 4/2001 |
| WO | 2001/042246 A2 | 6/2001 |
| WO | 2001/064655 A1 | 9/2001 |
| WO | 2001/081345 A1 | 11/2001 |
| WO | 2001/081346 | 11/2001 |
| WO | 2001/098344 A2 | 12/2001 |
| WO | 2002/000196 A2 | 1/2002 |
| WO | 2002/000661 A1 | 1/2002 |
| WO | 2002/046184 A1 | 6/2002 |
| WO | 2002/055084 A1 | 7/2002 |
| WO | 2002/055496 A1 | 7/2002 |
| WO | 2002/060492 A1 | 8/2002 |
| WO | 02/080926 | 10/2002 |
| WO | 2002/092573 A2 | 11/2002 |
| WO | 2002/096909 A1 | 12/2002 |
| WO | 2003/000688 | 1/2003 |
| WO | 2003/000695 A1 | 1/2003 |
| WO | 2003/011285 A1 | 2/2003 |
| WO | 2003/024967 A2 | 3/2003 |
| WO | 2003/037347 A1 | 5/2003 |
| WO | 2003/048162 A1 | 6/2003 |
| WO | 03/092595 | 11/2003 |
| WO | 2003/099771 A2 | 12/2003 |
| WO | 2003/099796 A1 | 12/2003 |
| WO | 2004/003026 A1 | 1/2004 |
| WO | 2004/005281 A1 | 1/2004 |
| WO | 2004/005282 A1 | 1/2004 |
| WO | 2004/026406 A1 | 4/2004 |
| WO | 2004/041814 A1 | 5/2004 |
| WO | 2004/046120 A2 | 6/2004 |
| WO | 2004/047843 A1 | 6/2004 |
| WO | 2004/056786 A2 | 7/2004 |
| WO | 2004/072063 A1 | 8/2004 |
| WO | 2004/080980 A1 | 9/2004 |
| WO | 2004/092154 A1 | 10/2004 |
| WO | 2004/099204 A1 | 11/2004 |
| WO | 2004/099205 A1 | 11/2004 |
| WO | 2005/005988 A2 | 1/2005 |
| WO | 2005/013986 A1 | 2/2005 |
| WO | 2005/020921 A2 | 3/2005 |
| WO | 2005/026129 A1 | 3/2005 |
| WO | 2005/028444 A1 | 3/2005 |
| WO | 2005/049033 A1 | 6/2005 |
| WO | 2005/051393 A1 | 6/2005 |
| WO | 2005/060972 A2 | 7/2005 |
| WO | 2005/061463 A1 | 7/2005 |
| WO | 2005/062795 A2 | 7/2005 |
| WO | 2005/089502 A2 | 9/2005 |
| WO | 2005/095400 A1 | 10/2005 |
| WO | 2005/105146 A1 | 11/2005 |
| WO | 2005/105814 A1 | 11/2005 |
| WO | 2005/105988 A2 | 11/2005 |
| WO | 2005/110410 A2 | 11/2005 |
| WO | 2005/117909 A2 | 12/2005 |
| WO | 2005/121130 A2 | 12/2005 |
| WO | 2005/123719 A1 | 12/2005 |
| WO | 2006/004984 A1 | 1/2006 |
| WO | 2006/136823 A1 | 1/2006 |
| WO | 2006/013114 A1 | 2/2006 |
| WO | 2006/022459 A1 | 3/2006 |
| WO | 2006/039718 A2 | 4/2006 |
| WO | 2006/046023 A1 | 5/2006 |

(56) References Cited

FOREIGN PATENT DOCUMENTS

| | | |
|---|---|---|
| WO | 2006/046024 A1 | 5/2006 |
| WO | 2006/052913 A1 | 5/2006 |
| WO | 2006/056399 A2 | 6/2006 |
| WO | 2006/067445 A2 | 6/2006 |
| WO | 2006/069080 A2 | 6/2006 |
| WO | 2006/077499 A1 | 7/2006 |
| WO | 2006/096270 A1 | 9/2006 |
| WO | 2006/101783 A2 | 9/2006 |
| WO | 2006/108103 A1 | 10/2006 |
| WO | 06/122806 | 11/2006 |
| WO | 2006/127587 A1 | 11/2006 |
| WO | 2006/129199 A1 | 12/2006 |
| WO | 2007/002433 A1 | 1/2007 |
| WO | 2007/025090 A2 | 3/2007 |
| WO | 2007/041130 A2 | 4/2007 |
| WO | 2007/043677 A1 | 4/2007 |
| WO | 2007/044050 | 4/2007 |
| WO | 2007/044894 A2 | 4/2007 |
| WO | 2007/049041 A1 | 5/2007 |
| WO | 2007/062459 A1 | 6/2007 |
| WO | 2007/070514 A1 | 6/2007 |
| WO | 2007/076423 A2 | 7/2007 |
| WO | 2007/077949 A1 | 7/2007 |
| WO | 2007/084557 A2 | 7/2007 |
| WO | 2007/090141 A2 | 8/2007 |
| WO | 2007/090748 A1 | 8/2007 |
| WO | 07/116313 | 10/2007 |
| WO | 2007/117494 A1 | 10/2007 |
| WO | 2007/129195 A2 | 11/2007 |
| WO | 2007/140222 A2 | 12/2007 |
| WO | 2008/013925 A2 | 1/2008 |
| WO | 2008/028937 A1 | 3/2008 |
| WO | 2008/035376 A2 | 3/2008 |
| WO | 2008/043031 A1 | 4/2008 |
| WO | 2008/058126 A2 | 5/2008 |
| WO | 2008/064157 A1 | 5/2008 |
| WO | 2008/067119 A2 | 6/2008 |
| WO | 2008/077712 A1 | 7/2008 |
| WO | 2008/079291 A2 | 7/2008 |
| WO | 2008/079292 A1 | 7/2008 |
| WO | 2008/082198 A1 | 7/2008 |
| WO | 2008/082839 A2 | 7/2008 |
| WO | 2008/082840 A1 | 7/2008 |
| WO | 2008/106692 A1 | 9/2008 |
| WO | 2008/124323 A1 | 10/2008 |
| WO | 2008/139161 A1 | 11/2008 |
| WO | 2008/145681 A2 | 12/2008 |
| WO | 2008/145688 A2 | 12/2008 |
| WO | 2008/157207 A2 | 12/2008 |
| WO | 2008/157208 A2 | 12/2008 |
| WO | 09/007839 | 1/2009 |
| WO | 2009/016460 A2 | 2/2009 |
| WO | 2009/049028 A1 | 4/2009 |
| WO | 2009/064486 A1 | 5/2009 |
| WO | 2009/064835 A1 | 5/2009 |
| WO | 2009/071577 A1 | 6/2009 |
| WO | 2009/100130 A1 | 8/2009 |
| WO | 2009/109576 A1 | 9/2009 |
| WO | 2009/114512 A1 | 9/2009 |
| WO | 2009/115572 A2 | 9/2009 |
| WO | 2009/158687 A1 | 12/2009 |
| WO | 2010/000978 A1 | 1/2010 |
| WO | 2010/001169 A2 | 1/2010 |
| WO | 2010/020905 A1 | 2/2010 |
| WO | 2010/022076 A1 | 2/2010 |
| WO | 2010/022081 A1 | 2/2010 |
| WO | 2010/026121 A1 | 3/2010 |
| WO | 2010/026122 A1 | 3/2010 |
| WO | 2010/026124 A1 | 3/2010 |
| WO | 10/039939 | 4/2010 |
| WO | 2010/081692 A1 | 7/2010 |
| WO | 2010/083283 A2 | 7/2010 |
| WO | 2010/135621 A1 | 11/2010 |
| WO | 2010/135650 A1 | 11/2010 |
| WO | 2011/025685 A1 | 3/2011 |
| WO | 2011/028685 A1 | 3/2011 |
| WO | 2011/029802 A1 | 3/2011 |
| WO | 2011/031554 A2 | 3/2011 |
| WO | 2011/035900 A1 | 3/2011 |
| WO | 2011/044481 A1 | 4/2011 |
| WO | 2011/057784 A1 | 5/2011 |
| WO | 2011/066369 | 6/2011 |
| WO | 2011/069141 A2 | 6/2011 |
| WO | 2011/112662 A | 9/2011 |
| WO | 2011/130146 A1 | 10/2011 |
| WO | 11/146808 | 11/2011 |
| WO | 2011/144338 A1 | 11/2011 |
| WO | 2012/003457 A1 | 1/2012 |
| WO | 2012/045010 | 4/2012 |
| WO | 2012/068440 A1 | 5/2012 |
| WO | 2012/068450 A1 | 5/2012 |
| WO | 2012/071612 | 6/2012 |
| WO | 12/177606 | 12/2012 |
| WO | 13/023119 | 2/2013 |
| WO | 13/026025 | 2/2013 |
| WO | 13/036611 | 3/2013 |
| WO | 13/173720 | 11/2013 |

OTHER PUBLICATIONS

Parks, "Tofacitinib and Other Kinase Inhibitors Offer New Approach io Treating Rheumatoid Arthritis," Rheumatologist, Jun. 2, 2013, pp. 1-12, Available from: [http://www.the-rheumatologist.org/details/article/4871781/Tofacitinib_and_Other_Kinase_Inhibitor_Offer_New_Approach_to_Treating_Rheumatoid.html], 12 pages.

Pedranzini et al., "Pyridone 6. A Pam-Janus-Activated Kinase Inhibitor, Induces Growth Inhibition of Multiple Myeloma Cells," Cancer Res., 2006, 66(19):9714-9721.

Puawani, Naresh et al., "Efficacy and safety of topical INCB018424, a selective Janus kinase 1 & 2 (JAK1&2) inhibitor in psoriasis," Journal of the American Academy of Dermatology, vol. 60, No. 3, 360 Park Avenue South, New York, NY 10010-1710 USA: Mosby-Elsevier, 2009.

Raza et al., "Novel insights into ths biology of myelodysplastic syndromes: excessive apoptosis and the role of cytokines," Int J Hematol, 1996, 63:265-278.

Raza et al., "The Myelodysplastic Syndrome in 1996: Complex Stem Cell Disorders Confounded by Dual Actions of cytokines," Leuk Res, 1996, 20:881-890.

Raza et al., "Phase 2 Study of lenalidomide in transfusion-dependent, low-risk, and intermediate-1 risk myelodysplastic syndromes with karyotypes other than deletion 5q," Blood, Jan. 2008, 111(1):86-93.

Reuters, "Jakafi (nxolitnib) improved advanced pancreas cancer outcomes in mid-stage trial," Internet Citation, Aug. 21, 2013, pp. 1-2, XP002717211, Retrieved from Internet: URL: http://www.curetoday.com/index.cfm/fuseaction/news.showNewsArticle/id/13/news_id/3785 [retrieved on Nov. 29, 2013].

Riese et al., "Inhibition of JAK kinases in patients with rheumatoid arthritis: scientific rationale and clinical outcomes," Best Practice & Research Clinical Rheumatology, 2010, 513-526.

Rollison, "Epidemiology of myelodysplastic syndrome and chronic myeloproliferative disorders in the United States, 2001-2004, using data from the NAACCR and SEER programs," Blood, Jul. 2008, 11(2):45-52.

Saemann et al., "Suppression of early T-cell-receptor-triggered cellular activation by the Janus kinase 3 Inhibitor MHI-P-154," Transplantation, 2003, 75(11):1864-1872.

Santini et al., "Hepcidin Levels and Their Determinants in Different Types of Myelodysplastic Syndromes," PLoS One, 2011, 6(8):e23109, pp. 1-8.

Schiffer, "Clinical issues in the management of patients with myelodysplasia," Hematology Am Soc Hematol Educ Program, 2006, 205-10.

Schiffer, "Myelodysplasia: the goodd, the fair and the ugly," Best Pract Res Clin Haematol, Mar. 2007, 20(1):49-55.

Schmidt et al., "Rituximab in an autoimmune bullous diseases: mixed responses and adverse effects," British Journal of Dermatology, 2007, 352-356.

(56) References Cited

OTHER PUBLICATIONS

Scott et al., (British Journal of Haematology), 148(6):944-947, Mar. 2010.
Silverman et al., "Further analysis of trials with azacitidine in patients with the myelodysplastic syndrome: studies 8421, 8921 and 9221 by the Cancer and Leukemia Group B," J Clin Oncol, Aug. 2006, 24(24):3895-903.
Silverman et al., "Randomized controlled trial of azacitidine in patients with the myelodysplastic syndrome: a study of the cancer and leukemia group B," J Clin Oncol, May 2002, 20(10):2429-40.
Sloand et al., "Factors affecting response and survival in patients with myelodysplasia treated with immunosuppressive therapy," J Clin Oncol, May 2008, 26(15):2505-11.
Song et al. "JAK1 Activates STAT3 Activity in Non-Small-Cell Lung Cancer Cells and IL-6 Neutralizing Antibodies can Suppress JAK1-STAT3 Signaling," Mol Cancer Ther., Mar. 2011, 10(3):481-94.
Spoerl et al., "Activity of therapeutic JAK 1/2 bioackade in graft-versus-host disease," Blood, 2014, 123(24):3832-3842.
Steensma el al., "The JAK2 V617F activating tyrosine kinase mutation is an infrequent event in both "atypical" myeloproliferative disorders and mylodysplastio syndromes," Blood, Aug. 2005, 106(4):1207-9.
Strassmann et al., "Suramin Interferes with Interleukin-6 Receptor Binding in Vitro and inhibits Colon-26-mediated Experimental Cancer Cachexia in Vivo," J. Clin. Invest., Nov. 1993, 92:2152-2159.
Symington et al., "The relationship of serum IL-6 levels to acute graft-versus-host disease and hepatorenal disease after human bone marrow transplantation," Transplantation, 1992, 54(3):457-462, (Abstract only).
Tamura et al., "Involvement of Human Interleukin 6 in Experimental Cachexia Induced by a Human Uterine Cervical Carcinoma Xenograft," Clin. Cancer Res., Nov. 1995, 1:1353-1358.
Ting et al., "The Synthesis of substituted bipiperidine amide compunds as CCR3 antagonists," Bioorg. Med. Chem. Lett., 2005, 15(5):1375-1378.
Trikha et al., "Targeted anti-interleukin-6 monoclonal antibody therapy for cancer: a review of ths rationale and clinical evidence," Clinical Cancer Research 2003, 9:4653-4665.
Vaillant et al., "Turbidity of pulpy fruit juice: A key factor for predicting cross-flow microfiltration performance," J Membrane Sci., 2008, 325:404-412.
Van Rhee et al., "Anti-Interleukin-6 Monoclonal man's Disease," J. Clin. Oncol, 2010, 28(23):3701-3708.
Vanhoute, "Selective JAK1 Inhibition in the Treatment of Rheumatoid Arthritis: Proof of Concept with GLPG0634," Arthritis Rheum, 2012, 64, 10:S1051-1.
Vardiman et al., "Atypical chronic myeloid leukaemia, BCR-ABL1 negative," in: Swerdlow, et al., WHO Classification of Tumors of Haematopoietic and Lymphoid Tissues (ed 4th). Lyon: IARC Press: 2008:80-81.
Vardiman et al., "The 2008 revision of the Word Health Organization (WHO) Classification of myeloid neoplasms and acute leukemia: rationale and important changes," Blood, 2009, 114:937-951.
Venugopal et al., "Special clinical concerns/problems in the management of MDS and secondary acute myeloid leukemias," Cancer Treat Res, 2001, 108:257-65.
Wang and Deisboeck, "Mathematical modeling in cancer drug discovery," Drug Discovery Today, 2014, 145-150.
WebMD. "Diabetes Health Center." Available at: <http://diabetes.webmd.com/guide/diabetestreatment_care>. 3 pages, retrieved from the Internet May 28, 2013.
Study of Ruxolitinib (INCB018424) Administered Orally to Patients with Androgen Independent Metastatic Prostate Cancer, Start date Feb. 2008.
A Study to Determine the Effect and Safely of an Oral Janus Kinase 2 (JAK2)-Inhibitor in Patients with Multiple Myeloma, Start date Mar. 2008.
Open Label Safety and Efficacy Study of Topical Investigational Drug to Treat Patients with Psoriasis, Start date Aug. 2007.
A Study Exploring the Safety, Tolerability, and Efficacy of a 4 Week Course of INCB018424 in Subjects with Active Rheumatoid Arthritis, Start date Oct. 2007.
Miyoshi et al., "Interleukin-8 concentrations in conjunctival epithelium brush cytology samples correlate with neutrophil, eosinophil infiltration, and corneal damage", Cornea, 2001, vol. 20, pp. 743-747.
Moreland, et al. "A Randomized Placebo-Controlled Study of INC8018424, a Selective Janus Kinase 1&2 (JAK 1&2) Inhibitor in Rheumatoid Arthritis (RA)" Presentation at the American College of Rheumatology meeting, Oct. 26, 2008. (20 pages).
Moriarty, et al., "The synthesis and SAR of 2-amino-pyrrolo[2,3-d]pyrimidines: A new class of Aurora-A kinase inhibitors," Bioorganic and Medicinal Chemistry Letters, 2006 vol. 16, No. 22, pp. 5778-5783.
Mosby's Dictionary of Medicine, Nursing, & Health Professions, sicca complex, 2009, Elsevier, printed from http://www.credoreference.com/entry/ehsmosbymed/sicca_complex, 2 pages.
Mullighan, et al, "JAK mutations in high-risk childhood acute lymphoblastic leukemia", Proc Natl Acad Sci USA. 2009, vol. 106, pp. 9414-9418.
Naka, "The paradigm of IL-6: from basic science to medicine", Arthritis Res. 2002, vol. 4, Suppl. 3, pp. S233-S242.
Nakagawara, Akira, "Trk receptor tyrosine kinases: A bridge between cancer and neural development." Cancer Letters, 2001, vol. 169, pp. 107-114.
Nally, et al., "Ocular discomfort and tear film break-up time in dry eye patients: A correlation", Invest Ophthalmol Vis Sci, 2000, vol. 41, No. 4, pp. 1436 (Poster Presentation).
Naqvi, et al., "A potential rote of ruxolitinib in leukemia", Expert Opinion on Investigational Drugs, 2011, vol. 20, No. 8, pp. 1159-1166.
National Cancer Institute, "FDA Approval for Ruxolitinib Phosphate", http://www.cancergovicancertopics/druginfo/fda-ruxolitinibphosphate posted Nov. 18, 2011 (3 pages).
Naus, et al., "6-(Het)aryl-7-Deazapurine Ribonucleosides as Novel Potent Cytostatic Agents", J. Med. Chem., 2010, vol. 53, No. 1, pp. 460-470.
Neidle, "Chapter 18: Failure modes in anticancer drug discovery and development" in Cancer Drug Discovery and Design (Elsevier/Academic Press, 2008), pp. 427-431.
Nelson, et al., "Tear film osmolality determination: an evaluation of potential errors in measurement" Curr Eye Res, 1986, vol. 5, No. 9, pp. 677-681.
Neubauer, H., et al., "Jak2 Deficiency Defines an Essential Developmental Checkpoint in Definitive Hematopoiesis", Cell. 1998. vol. 93, No. 3, pp. 397-409.
Nicholoff, et al., "Recent Insights into the immunopathogenesis of psoriasis provide new therapeutic opportunities", J. Clin. Invest., 2004, vol. 113, pp. 1664-1675.
Nichols, et al., "The lack of association between signs and symptoms in patients with dry eye disease", Cornea, 2004, vol. 23, No. 8, pp. 762-770.
Nichols, et al., "The repeatability of clinical measurements of dry eye", Cornea, 2004, vol. 23, No. 3, pp. 272-285.
Nishio, et al., "Tyrosine kinase-dependent modulation by interferon-a of the ATP-sensitive K+current in rabbit ventricular myocytes", FEBS Letters, 1999, vol. 445, pp. 87-91.
Nitta, et al., "Peptide-Titanium Complex as Catalyst for Asymmetric Addition of Hydrogen Cyanide to Aldehyde", J. Am. Chem. Soc., 1992, vol. 114, pp. 7969-7975.
Norn, M "Quantitative tear ferning. Clinical investigations", Acta Ophthalmol (Copenh), 1994, vol. 72, No. 3, pp. 369-372.
Oguz, et al., "The height and radius of the tear meniscus and methods for examining these parameters", Cornea, 2000, vol. 19, pp. 497-500.
Ortmann, et al., "Janus kinases and signal transducers and activators of transcription: their roles in cytokine signaling, development and immunoregulation." Arthritis Res, 2(1): 16-32 (2000).
Ostojic, et al., "Ruxolitinib for the treatment of myelofibrosis", Drugs of Today, 2011, vol. 47, No. 11, pp. 817-827.

(56) References Cited

OTHER PUBLICATIONS

Ousler, et al., "Factors that influence the inter-blink interval (IB) as measured by the ocular protection index (OPI)", Invest Ophthalmol Vis Sci 2001; 43: E-abstract 56 (Poster presentation) ARVO (2002) 2 pages, downloaded from http://abstracts.iov.s.org/cgi/content/abstract/43/12/56?maxtoshow on Aug. 14, 2009.
Palmer, et al., "Multiple roles of ephrins in morphogenesis, neuronal networking, and brain function." Genes & Dev., 2003, vol. 17, pp. 1429-1450.
Pardanani, "JAK2 inhibitor therapy in myeloproliferative disorders: rationale, preclinical studies and ongoing clinical trialsJAK2 inhibitor therapy in MPD", Leukemia 2008, vol. 22, pp. 23-30.
Parganas, et al., "Jak2 is Essential for Signaling through a Variety of Cytokine Receptors", Cell, 1998, vol. 93, No. 3, pp. 385-395.
Park et al., "Homogeneous Proximity Tyrosine Kinase Assays: Scintillation Proximity Assay versus Homogeneous Time-Resolved Fiuorescense", Analytical Biochemistry, 1999, vol. 269, pp. 94-104.
Patani, et al., "Bioisosterism: A Rational Approach in Drug Design", Chem. Rev., 1996, vol. 96, pp. 3147-3176.
Patrick, "An Introduction to medicinal chemistry" Oxford University Press Inc., New York (31 pages) (cited in Opposition from India dated Nov. 12, 2012.
Pearce et al., "Spatial location studies on the chemical composition of human tear ferns", Ophthalmic Physiol Opt, 2000, vol. 20, No. 4, pp. 306-313.
Pearce, et al., "An improved fluorophotometrio method for tear turnover assessment", Optom Vis Sci, 2001, vol. 78No. 1, pp. 30-36.
Pensyl, et al., "The repeatability of tear mucus ferning grading", Optom Vis Sci, 1998, vol. 75, No. 8, pp. 600-604.
Pernis, et al., "JAK-STAT signaling in asthma." J Clin Invest, 2002, vol. 109, No. 10, pp. 1279-1283 (2002).
Pflugfelder, et al., "Evaluation of subjective assessments and objective diagnostic tests for diagnosing tear-film disorders known to cause ocular irritation", Cornea, 1998, vol. 17, No. 1, pp. 38-56.
Pillonel, "Evaluation of phenylaminopyrimidines as antifungal protein kinase inhibitors", Pest Management Science, 2005, vol. 61, pp. 1069-1076.
Pirard, B. et al., "Classification of Kinase Inhibitors Using BCUT Descriptors", J. Chem. Inf. Comput. Sci., 2000, vol. 40, pp. 1431-1440.
Pisella, et al., Conjunctival proicftammatory and proapoptotic effects of latanoprost, preserved timolol and unpreserved timolol: an ex vivo and in vitro study, Invest Ophthalmol Vis Sci, 2004, vol. 45, pp. 1360-1368.
Pisella, et al., Flow cytometric analysis of conjunctival epithelium in ocular rosacea and keratoconjunctivitis sicca. Ophthalmology, 2000, vol. 107, pp. 1841-1849.
Portnaya, et al., "Azomethine dyes. IV. Indoaniline dyes derived from heterocyclic N-substituted 1-hydroxy-2-naphthamid", Ts Vses Nauchn Issled Kinofotoinst, 1960, No. 40, pp. 106-108 (with English abstract 20 pages total).
Press Release dated Sep. 18, 2008: "Incyte's Topical JAK Inhibitor Demonstrates Positive Proof-of-Concept Results in Patients with Mild to Moderate Psoriasis" (4 pages).
Prezent, et al., "Boron chelates as intermediates in the synthesis of new functionalized pyridines and pyrimidines from a, a-dioxoketene aminals", Proceedings of the International Conference on the Chemistry of Boron, 2003, vol. 11 (abstract only—1 page).
Punwani et al., Poster/presentation, "Initial Efficacy and Safety of Topical INCYB018424 Cream, a Selective Janus Kinase 1&2 (JAK 1&2) Inhibitor in Psoriasis" 17th Congress of the European Academy of Dermatology and Venereology, Paris, France, Sep. 17, 2008 (15 pages).
Quesada et al., "One-pot conversion of activated alcohols into 1,1-dibromoalkenes and terminal alkynes using tandem oxidation processes with manganese dioxide", Tetrahedron, 2006, vol. 62, pp. 6673-6680.
Quintas-Cardama, et al., "Preclinical characterization of the selective JAK1/2 inhibitor INCB018424: therapeutic implications for the treatment of myeloproliferative neoplasms", Blood First Edition Paper, pre-published online Feb. 3, 2010, American Society of Hematology.
Ravin, "Preformulation", Remington's Pharmaceutical Sciences, 17th ed., Mack Publishing Company, Easton, Pa., 1985, Chapter 76, pp. 1469-1423.
Ren et al., "Compounds and Compositions as Protein Kinase Inhibitors," U.S. Appl. No. 60/578,491, filed Jun. 10, 2004 (56 pages).
Research Gate, "What is the difference between Ex vivo and In vitro?", Dec. 18, 2014, available at http://www.resarchgate.net/postNVhat_is_the_difference_between_Ex_vivo_and_in_vitro, 6 pages.
Roberts, et al., "Trends in the Risks and Benefits to Patients with Cancer Participating in Phase I Clinical Trials", JAMA 2004, vol. 292, No, 17, pp. 2130-2140.
U.S. Appl. No. 12/137,883 / 2008/0312258 / U.S. Pat. No. 7,834,022, filed Jun. 12, 2008 / Dec. 18, 2008 / Nov. 16, 2010, James D. Rodgers.
U.S. Appl. No. 12/900,180 / 2011/0082159 / U.S. Pat. No. 8,889,697, filed Oct. 7, 2010 / Apr. 7, 2011 / Nov. 18, 2014, James D. Rodgers.
U.S. Appl. No. 14/518,419 / 2015/0164900, filed Oct. 20, 2014 / Jun. 18, 2015, James D. Rodgers.
U.S. Appl. No. 15/496,824 / 2017/0326144 / U.S. Pat. No. 10,463,667, filed Apr. 25, 2017 / Nov. 16, 2017 / Nov. 5, 2019, James D. Rodgers.
U.S. Appl. No. 16/583,938 / 2020/0038404, filed Sep. 26, 2019 / Feb. 6, 2020, James D. Rodgers.
U.S. Appl. No. 12/137,892 / 2008/0312259, filed Jun. 12, 2008 / Dec. 18, 2008, James D. Rodgers.
U.S. Appl. No. 14/097,588 / 2014/0094476 / U.S. Pat. No. 8,722,693, filed Dec. 5, 2013 / Apr. 3, 2014 / May 13, 2014, James D. Rodgers.
U.S. Appl. No. 14/097,598 / 2014/0094477, filed Dec. 5, 2013 / Apr. 3, 2014, James D. Rodgers.
U.S. Appl. No. 14/256,311 / U.S. Pat. No. 8,829,013, filed Apr. 18, 2014 / Sep. 9, 2014, James D. Rodgers.
U.S. Appl. No. 14/256,383 / U.S. Pat. No. 8,822,481, filed Apr. 18, 2014 / Sep. 2, 2014, James D. Rodgers.
U.S. Appl. No. 14/270,915 / 2014/0303196 / U.S. Pat. No. 9,376,439, filed May 6, 2014 / Oct. 9, 2014 / Jun. 28, 2016, James D. Rodgers.
U.S. Appl. No. 15/164,518 / 2016/0339031 / U.S. Pat. No. 10,016,429, filed May 25, 2016 / Nov. 24, 2016 / Jul. 10, 2018, James D. Rodgers.
U.S. Appl. No. 16/003,210 / 2019/0046534 / U.S. Pat. No. 10,610,530, filed Jun. 8, 2018 / Feb. 14, 2019 / Apr. 7, 2020, Hui-Yin Li.
U.S. Appl. No. 16/806,244 / 2020/0197401, filed Mar. 2, 2020 / Jun. 25, 2020, Hui-Yin Li.
U.S. Appl. No. 12/687,623 / 2010/0190981 / U.S. Pat. No. 8,410,265, fileld Jan. 14, 2010 / Jul. 29, 2010 / Apr. 2, 2013, Jiacheng Zhou.
U.S. Appl. No. 13/761,742 / 2013/0253190 / U.S. Pat. No. 9,000,161, filed Feb. 7, 2013 / Sep. 26, 2013 / Apr. 7, 2015, Jiacheng Zhou.
U.S. Appl. No. 13/761,771 / 2013/0253191 / U.S. Pat. No. 8,883,806, filed Feb. 7, 2013 / Sep. 26, 2013 / Nov. 11, 2014 / Jiacheng Zhou.
U.S. Appl. No. 13/761,830 / 2013/0253193 / U.S. Pat. No. 8,993,582, filed Feb. 7, 2013 / Sep. 26, 2013 / Mar. 31, 2015, Jiacheng Zhou.
U.S. Appl. No. 14/593,688 / 2015/0218174 / U.S. Pat. No. 9,290,506, filed Jan. 9, 2015 / Aug. 6, 2015 / Mar. 22, 2016, Jiacheng Zhou.
U.S. Appl. No. 15/016,918 / 2016/0257687 / U.S. Pat. No. 9,908,888, filed Feb. 5, 2016 / Sep. 8, 2016 / Mar. 6, 2018, Jiacheng Zhou.
U.S. Appl. No. 15/869,650 / 2018/0237442 / U.S. Pat. No. 10,364,248, filed Jan. 12, 2018 / Aug. 23, 2018 / Jul. 30, 2019, Jiacheng Zhou.
U.S. Appl. No. 16/436,195 / 2020/002341 /, filed Jun. 10, 2019 / Jan. 2, 2020, Jiacheng Zhou.
U.S. Appl. No. 12/901,001 / 2011/0086810 / U.S. Pat. No. 8,486,902, filed Oct. 8, 2010 / Apr. 14, 2011 / Jul. 16, 2014, James D. Rodgers.
U.S. Appl. No. 13/917,124 / 2013/0345157 / U.S. Pat. No. 8,748,401, filed Jun. 13, 2013 / Dec. 26, 2013 / Jun. 10, 2014, James D. Rodgers.
U.S. Appl. No. 14/263,476 / 2014/0378400, filed Apr. 28, 2014 / Dec. 25, 2014, James D. Rodgers.
U.S. Appl. No. 13/030,682 / 2011/0207754, filed Feb. 18, 2011 / Aug. 25, 2011, Yun-Long Li.
U.S. Appl. No. 14/499,916 / 2015/0087662, filed Sep. 29, 2014 / Mar. 26, 2015, Yun-Long Li.

(56) References Cited

OTHER PUBLICATIONS

U.S. Appl. No. 13/399,274 / 2012/0214825, filed Feb. 17, 2012 / Aug. 23, 2012, Alessandro M. Vannucchi.
U.S. Appl. No. 13/571,525 / 2013/0040973 / U.S. Pat. No. 9,358,229, filed Aug. 10, 2012 / Feb. 14, 2013 / Jun. 7, 2016, Alessandro M. Vannucchi.
U.S. Appl. No. 11/115,702 / 2006/0106020, filed Apr. 27, 2005 / May 18, 2006, James D. Rodgers.
U.S. Appl. No. 12/187,061 / 2009/0215766 / filed Aug. 6, 2008 / Aug. 27, 2009, James D. Rodgers.
U.S. Appl. No. 11/313,394 / 2006/0183906 / U.S. Pat. No. 7,335,667, filed Dec. 21, 2005 / Aug. 17, 2006 / Feb. 26, 2008, James D. Rodgers.
U.S. Appl. No. 11/980,314 / 2011/0086835 / U.S. Pat. No. 8,053,433, filed Oct. 30, 2007, Apr. 14, 2011 / Nov. 8, 2011, James D. Rodgers.
U.S. Appl. No. 13/245,333 / 2012/0014989 / U.S. Pat. No. 8,445,488, filed Sep. 26, 2011 / Jan. 19, 2012 / May 21, 2013, James D. Rodgers.
U.S. Appl. No. 13/889,618 / 2013/0296299 / U.S. Pat. No. 8,741,895, filed May 8, 2013 / Nov. 7, 2013 / Jun. 3, 2014, James D. Rodgers.
U.S. Appl. No. 14/255,092 / 2014/0228346 / U.S. Pat. No. 9,090,611, filed Apr. 17, 2014 / Aug. 14, 2014 / Jul. 28, 2015, James D. Rodgers.
U.S. Appl. No. 14/799,777 2015/0315185, filed Jul. 15, 2015/Nov. 5, 2015, James D. Rodgers.
U.S. Appl. No. 11/637,545 / 2007/0135461 / U.S. Pat. No. 7,598,257, filed Dec. 12, 2006 / Jun. 14, 2007 / Oct. 6, 2009, James D. Rodgers.
U.S. Appl. No. 12/138,082 / 2009/0181959 / U.S. Pat. No. 8,415,362, filed Jun. 12, 2008 / Jul. 16, 2009 / Apr. 9, 2013, James D. Rodgers.
U.S. Appl. No. 13/754,533 / 2013/0137681, filed Jan. 30, 2013 / May 30, 2013, James D. Rodgers.
U.S. Appl. No. 12/549,170 / 2010/0022522 / U.S. Pat. No. 8,541,425, filed Aug. 27, 2009 / Jan. 28, 2010 / Sep. 24, 2013, James D. Rodgers.
U.S. Appl. No. 13/076,176 / 2011/0224157 / U.S. Pat. No. 8,946,245, filed Mar. 30, 2011 / Sep. 15, 2011 / Feb. 3, 2015, James D. Rodgers.
U.S. Appl. No. 13/076,220 / 2011/0223210 / U.S. Pat. No. 8,530,485, filed Mar. 30, 2011 / Sep. 15, 2011 / Sep. 10, 2013, James D. Rodgers.
U.S. Appl. No. 14/020,505 / 2014/0005210 / U.S. Pat. No. 9,206,187, filed Sep. 6, 2013 / Jan. 2, 2014 / Dec. 8, 2015, James D. Rodgers.
U.S. Appl. No. 14/274,948 / 2014/0243360 / U.S. Pat. No. 9,079,912, filed May 12, 2014 / Aug. 28, 2014 / Jul. 14, 2015, James D. Rodgers.
U.S. Appl. No. 14/711,576 / 2015/0238492, filed May 13, 2015 / Aug. 27, 2015, James D. Rodgers.
U.S. Appl. No. 15/173,057, filed Jun. 3, 2016, James D. Rodgers.
U.S. Appl. No. 15/233,652, filed Aug. 10, 2016, James D. Rodgers.
U.S. Appl. No. 14/033,039 / 2014/0018374 / U.S. Pat. No. 8,933,086, filed Sep. 20, 2013 / Jan. 16, 2014 / Jan. 13, 2015, James D. Rodgers.
U.S. Appl. No. 11/961,424 / 2008/0188500 / U.S. Pat. No. 8,513,270, filed Dec. 20, 2007 / Aug. 7, 2008 / Aug. 20, 2013, Argyrios G. Arvanitis.
U.S. Appl. No. 13/834,040 / 2013/0274257 / U.S. Pat. No. 8,841,318, filed Mar. 15, 2013 / Oct. 17, 2013 / Sep. 23, 2014, Argyrios G. Arvanitis.
U.S. Appl. No. 12/270,135 / 2009/0318405 / U.S. Pat. No. 8,309,718, filed Nov. 13, 2008 / Dec. 24, 2009 / Nov. 13, 2012, Yun-Long Li.
U.S. Appl. No. 12/401,348 / 2009/0233903 / U.S. Pat. No. 8,158,616, filed Mar. 10, 2009 / Sep. 17, 2009 / Apr. 17, 2012, James D. Rodgers.
U.S. Appl. No. 13/315,750 / 2012/0077798 / U.S. Pat. No. 8,420,629, filed Dec. 9, 2011 / Sep. 17, 2009 / Apr. 16, 2013, James D. Rodgers.
U.S. Appl. No. 13/853,475 / 2013/0225556, filed Mar. 29, 2013 / Aug. 29, 2013, James D. Rodgers.
U.S. Appl. No. 11/524,641 / 2007/0149506, filed Sep. 21, 2006 / Jun. 28, 2007, Argyrios G. Arvanitis.
U.S. Appl. No. 12/418,132 / 2009/0197869, filed Apr. 3, 2009 / Aug. 6, 2009, Argyrios G. Arvanitis.
U.S. Appl. No. 13/479,045 / 2012/0329782 / U.S. Pat. No. 8,563,541, filed May 23, 2012 / Dec. 27, 2012 / Oct. 22, 2013, Argyrios G. Arvanitis.
U.S. Appl. No. 14/032,629 / 2014/0031344 / U.S. Pat. No. 8,835,423, filed Sep. 20, 2013 / Jan. 30, 2014 / Sep. 16, 2014, Argyrios G. Arvanitis.
U.S. Appl. No. 12/571,834 / 2010/0113416, filed Oct. 1, 2009 / May 6, 2010, Paul A. Friedman.
U.S. Appl. No. 13/564,271 / 2012/0301464, filed Aug. 1, 2012 / Nov. 29, 2012, Paul A. Friedman.
U.S. Appl. No. 15/156,125, filed May 16, 2016, Paul A. Friedman.
U.S. Appl. No. 12/784,916 / 2010/0298334 / U.S. Pat. No. 8,716,303, filed May 21, 2010 / Nov. 25, 2010 / May 6, 2014, James D. Rodgers.
U.S. Appl. No. 14/250,843 / 2014/0221379 / U.S. Pat. No. 9,334,274, filed Apr. 11, 2014 / Aug. 7, 2014 / May 10, 2016, James D. Rodgers.
U.S. Appl. No. 12/785,057 / 2010/0298355 / U.S. Pat. No. 8,604,043, filed May 21, 2010 / Nov. 25, 2010 / Dec. 10, 2013, Yun-Long Li.
U.S. Appl. No. 14/075,209 / 2014/0073657 / U.S. Pat. No. 9,216,984, filed Nov. 8, 2013 / Mar. 13, 2014 / Dec. 22, 2015, Yun-Long Li.
U.S. Appl. No. 14/943,734 / 2016/0067253, filed Nov. 17, 2015 / Mar. 10, 2016, Yun-Long Li.
U.S. Appl. No. 12/872,925 / 2011/0059951 / U.S. Pat. No. 9,249,145, filed Aug. 31, 2010 / Mar. 10, 2011 / Feb. 2, 2016, James D. Rodgers.
U.S. Appl. No. 13/043,986 / 2011/0224190 / U.S. Pat. No. 8,765,734, filed Mar. 9, 2011 / Sep. 15, 2011 / Jul. 1, 2014, Taisheng Huang.
U.S. Appl. No. 14/289,121 / 2014/0275031, filed May 28, 2014 / Sep. 18, 2014, Taisheng Huang.
U.S. Appl. No. 13/112,370 / 2011/0288107, filed May 20, 2011 / Nov. 24, 2011, Bhavnish Parikh.
U.S. Appl. No. 14/714,820 / 2015/0250790, filed May 18, 2015 / Sep. 10, 2015, Bhavnish Parikh.
U.S. Appl. No. 13/300,094 / 2012/0149681 / U.S. Pat. No. 8,933,085, filed Nov. 18, 2011 / Jun. 14, 2012 / Jan. 13, 2015, James D. Rodgers.
U.S. Appl. No. 14/556,775 / 2015/0087632, filed Dec. 1, 2014 / Mar. 26, 2015, James D. Rodgers.
U.S. Appl. No. 13/300,137 / 2012/0149682 / U.S. Pat. No. 9,034,884, filed Nov. 18, 2011 / Jun. 14, 2012 / May 19, 2015, James D. Rodgers.
U.S. Appl. No. 13/526,957 / 2013/0018034 / U.S. Pat. No. 8,691,807, filed Jun. 19, 2012 / Jan. 17, 2013 / Apr. 8, 2014, Wenqing Yao.
U.S. Appl. No. 14/186,338 / 2014/0171409 / U.S. Pat. No. 9,023,840, filed Feb. 21, 2014 / Jun. 19, 2014 / May 5, 2015, Wenqing Yao.
U.S. Appl. No. 14/697,236 / 2015/0225411, filed Apr. 27, 2015 / Aug. 13, 2015, Wenqing Yao.
U.S. Appl. No. 13/588,776 / 2013/0045963 / U.S. Pat. No. 9,359,358, filed Aug. 17, 2012 / Feb. 21, 2013 / Jun. 7, 2016, James D. Rodgers.
U.S. Appl. No. 13/605,331 / 2013/0060026, filed Sep. 6, 2012 / U.S. Appl. No. 13/605,331, Jiacheng Zhou.
Response to Office Action corresponding to U.S. Appl. No. 11/115,702, dated Nov. 19, 2007, 7 pgs.
Response to Restriction Requirement corresponding to U.S. Appl. No. 11/115,702, dated May 29, 2007, 8 pgs.
Restriction Requirement corresponding to U.S. Appl. No. 11/115,702, dated Mar. 6, 2007, 6 pgs.
Gould, P.S. "Salt selection for basic drugs", Int J Phamaceutics 1986, 33, pp. 201-217.
Black, S. N., et al., "Structure, Solubility, Screening, and Synthesis of Molecular Salts", J Pharm Sci May 2007, 96, pp. 1053-1068.
Steffen Paulekuhn, G., et al., "Trends in active pharmaceutical ingredient salt selection based on analysis of the orange book database", J. Med. Chem., Dec. 2007, 50, pp. 6665-6672.
Bastin, R.J., et al., "Salt selection and optimization procedures for pharmaceutical new chemical entities", Organic Process Research & Development 2000,4n pp. 427-435 Sep. 6, 2019.
Notice of Opposition in corresponding European Patent No. 3070090, filed Sep. 6, 2019.
26th Annual JPMorgan Healthcare Conference presentation dated Jan. 8, 2008 (28 pages).

(56) References Cited

OTHER PUBLICATIONS

Abe, et al., "Effective Methods for Introducing Some Aryl and Heteroaryl Substituent onto 1-Azaazulene Nuclei", Heterocycles, 2005, vol. 66, pp. 229-240.
Abelson, et al., "Alternate reference values for tear film break-up time in normal and dry eye populations, Lacrimal Gland, Tear Film, and Dry Eye Syndromes 3 Part B", Adv Exp Med Biol, 2002, vol. 506, pp. 1121-1125.
Abelson, et al. "Dry eye syndrome: diagnosis, clinical trials, and pharmaceutical treatmenrimproving clinical trials. Lacrimal Gland, Tear Film, and Dry Eye Syndromes 3 Part B", Adv Exp Med Biol, 2002, vol. 506, pp. 1079-1086.
Abstract of Chilean patent application No. 3496-06 published in Official Gazette of the Republic of Chile (Jun. 1, 2007) and publication (2 pages).
Aho. et al., Expression of human pim family genes is selectively up-regulaled by cytokines promoting T helper type 1, but not T helper type 2, cell differentiation, Immunology 2005, vol. 116, pp. 82-88.
Albach, et al., "Diagnosis of keratoconjunctivitis sicca in rheumatoid arthritis. The value of various tests", Ophthalmologe, 1994, vol. 91, No. 2, pp. 229-234—in German (with English abstract/sumnmary contained therein).
Anderson et al., "Biochemical characterization of GSK1070916, a potent and selective inhibitor of Aurora B and Aurora C kinases with an extremely tong residence time", Biochem, J., 2009, vol. 420, No. 2, pp. 259-265.
Bachmann, et al., "The serine/thrsonine kinease Pim-1," The International Journal of Biochechemistry and Cell Biology 2005, vol. 37, pp. 726-730.
Banker and Rhodes: Eds. "Prodrugs" from Modern Pharmaceutics, Marcel Dekker. Inc.: New York, NY: pp. 596 (1996).
Barabino et al., "Tear film and ocular surface tests in animal models of dry eye; uses and limitations", Experimental Eye Research, 2004, vol. 79, pp. 613-621.
Barr, et al., "Corneal scarring in ths Collaborative Longitudinal Evaluation of Keratoconus (CLEK) Study: baseline prevalence and repeatability of detection", Cornea, 1999, vol. 18, No. 1, pp. 34-46.
Baudouin et al., "Flow cytometry in impresston cytology specimens. A new method for evaluation of conjunctival Inflammation", Invest Ophthalmol Vis Sci, 1997, vol. 38, pp. 1458-1464.
Baylel, et al., "The human Pim-2 proto-oncogene and its testicular expression" Biochimica et Biophysica Acta 1998, vol. 1442, pp. 274-285.
Begley, et al., "Use of the dry eye questionnaire to measure symptoms of ocular irritation in patients with aqueous tear deficient dry eye", Cornea, 2002, vol. 21, pp. 664-670.
Bell, Malcolm, and Zalay, Andrew, "Synthesis of Substituted 3-Amino[6,5-b] triazinoindoles." Journal of Heterocyclic Chemistry, 1975, vol. 12, No. 5, pp. 1001-1004.
Berge, et al., "Pharmaceutical salts", J. Pharma. Science, 1977, vol. 66, No. 1, pp. 1-19.
Beyer, "Uber die Synthese von 2-Methylmercapto-1.3.4-thiodiazinen und deren Umlagerung in Pyrazoidesivate (The synthesis of 2-methylthio-1,3,4-thiadiazines and their rearrangement to pyrazole derivatives)", Chem. Berichte Jahrg., 1959, vol. 92, pp. 2593-2599 (abstract provided).
Bhovi, et al., "1 ,3-Dipolar Cycloaddition Reaction: Synthesis and Antimicrobial, Activity of Some New 3-Ethoxycarbonyl-s-Methoxy-6-Bromo-2-Triazolylmethylindoles", Indian Journal of Heterocyclic Chemistry, 2004, vol. 14, pp. 15-18.
Blume-Jensen, et al, "Oncogenic kinase signaling", Nature 2001, vol. 411, No. 6835, pp. 355-365.
Borie, et al., "Combined Use of the Jak3 inhibitor CP-690, 550 with Mycophenolate Mofetil to Prevent Kidney Allograft Rejection in Nonhuman Primates", Transplantation, 2005, vol. 80, No. 12, pp. 1756-1764.
Bolen, "Nonreceptor tyrosine protein kinases", Oncogene, 1993, vol. 8, No. 8, pp. 2025-2031.

Bollrath et al., "gp130-Mediated Stat3 Activation In Enterocytes Regulates Cell Survival and Cell-Cycle Progression during Colitis-Associated Tumorigenesis," Cancer Cell, 2009, vol. 15, pp. 91-102.
Bosworth, JAK1/IAK2 Inhibitor Ruxolitinib Is a Rising Start, Clinical Oncology, 2011, vol. 06, No. 04 (3 pages).
Boudny, et al., "JAK/STAT signaling pathways and cancer", Neoplasm, 2002, vol. 49, pp. 349-355.
Bourcier, et al., "Expression of CD40 and CD40 ligand in the human conjunctival epithelium", Invest Ophthalmol Vis Sci, 2000, vol. 41, pp. 120-126.
Bowman, et al. "STATs in oncogenesis". Oncogene, 2000, vol. 19, pp. 2474-2488.
Brignole, et al., "Expression of Fas-Fas Ligand Antigens and Apoptotic Marker APO2-7 by the Human Conjunctival Epithelium. Positive correlation with class II HLA DR expression in Inflammatory Ocular Surface Disorders", Exp Eye Res, 1998, vol. 67, pp. 667-697.
Brignole, et al., "Flow cytometric analysis of inflammatory markers in conjunctival epithelial cells of patients with dry eyes", Invest Ophthalmol Vis Sci. 2000, vol. 41, pp. 1356-1363.
Brignole, et al., "Flow cytometric analysis of inflammatory markers in KCS: 6-month treatment with topical cyclosporin A", Invest Ophthalmol Vis Sci, 2001, vol. 42, pp. 90-95.
Brignole, et al., "Flow cytometry in conjunctiva impression cytology: a new tool for exploring ocular surface pathologies", Exp Eye Res, 2004, vol. 78, pp. 473-481.
Bromberg et al., "Inflammation and Cancer: IL-6 and STAT3 Complete the Link," Cancer Cell. 2009, vol. 15, pp. 79-80.
Bron, et al., "Grading of corneal and conjunctival staining in the context of other dry eye tests", Cornea, 2003, vol. 22, No. 7, pp. 640-650.
Bron, et al., "Methodologies to Diagnose and Monitor Dry Eye Disease: Report of the Diagnostic Methodology Subcommittee of the International Dry Eye Workshop (2007)", The Ocular Surface, 2007, vol. 5, No. 2, pp. 108-152.
Burger, et al., "Gp130 and ras mediated signaling in human plasma cell line IN/a-6: a cytokine-regulated tumor model for plasmacytoma", Hematol J., 2001, vol. 2, pp. 42-53.
Burger, et al., "Janus kinase inhibitor INCB20 has antiproliferative and apoptotic effects on human myeloma cells in vitro and in vivo", Mol. Cancer Ther. 2009, vol. 8, No. 1, pp. 26-35.
Campas-Moya, "Ruxolitinib. Tyrosine-protein kinase JAK1/2 inhibitor, treatment of myelofibrosis, treatment of myeloproliferative neoplasms, treatment of psoriasis", Drugs of the Future, 2010, vol. 35, No. 6, pp. 457-465.
Candotti, et al. "Molecular aspects of primary immuno-deficiencies: lessons from cytokine and other signaling pathways.", J Clin Invest, 2002, vol. 109, No. 10, pp. 1261-1269.
Candotti, et al. "Structural and functional basis for JAK3-deficient severe combined immunodeficiency.", Blood, 1997, vol. 90, No. 10, pp. 3996-4003.
Carey and Sundberg, Advanced Organic Chemistry, Part B: Reactions and Synthesis, 4th ed., Kluwer Academic/Plenum Publishers:New York, pp. 111-119 (2001)
Carey and Sundberg, Advanced Organic Chemistry, Part B: Reactions and Synthesis, Oxidations, 4th ed., Kluwer Academic/Plenum Publishers:New York, 2001, pp. 747-757.
Cermak, et al, "Is complete androgen insensitivity syndrome associated with alterations in the meibomium gland and ocular surface", Cornea, 2003, vol. 22, pp. 516-521.
Cetkovic-Cvrlje, et al. "Targeting JAK3 with JANEX-1 for prevention of autoimmune type 1 diabetes in NOD mice.", Clin Immunol, 2003, vol. 106, No. 3, pp. 213-225.
Chelandon, "Targeting mutated protein tyrosine kinases and their signaling pathways in hematologic malignancies", Haematologica, 2005, vol. 90, No. 7, pp. 949-968.
Changelian, et al., "Prevention of Organ Allograft Rejection by a Specific Janus Kinase 3 Inhibitor", Science, 2003, vol. 302, pp. 875-878.
Chauhan, et al., "Autoimmunity in Dry Eye due to resistance of Th17 to Treg Suppression", J. Immunology, 2009, vol. 182, No. 3, pp. 1247-1252.

(56) References Cited

OTHER PUBLICATIONS

Chen, et al., "Stat3 Activation in Human Endometrial and Cervical Cancer", British Journal of Cancer, 2007, vol. 96, pp. 591-599.
Chew, et al., "An instrument for quantifying meibomian lipid on the lid margin: the Meibometer", Curr Eye Res, 1993a, vol. 12, pp. 247-254.
Chew, et al., "The casual level of meibomian lipids in humans", Current Eye Research, 1993b, vol. 12, pp. 255-259.
Goto, et al., "Differentiation of lipid tear deficiency dry eye by kinetic analysis of fear interference images", Arch Ophthalmol, 2003, vol. 121, pp. 173-180.
Goto, et al., Kinetic analysis of tear interference images in aqueous tear deficiency dry eye before and after punctal occlusion. Invest Ophthalmol Vis Sci, 2003, vol. 44, pp. 1897-1905.
Goto, et al., "Tear Film Stability Analysis System: Introducing a new applicatian for videokeratography", Cornea, 2004a, vol. 3, No. 8, pp. S65-S70.
Gottlieb, A.B., et al. "Psoriasis: Emerging Therapeutic Strategies", Nat Rev Drug Disc., 2005, vol. 4, pp. 19-34.
Grabbe, et al., "Immunoregulatory mechanisms involved in elicitation of allergic—contact hypersensitivity", Immunol Today, 1998, vol. 19, No. 1, pp. 37-44 (only 1 page provide and marked "best available copy").
Gregory, et al., "Clinical and laboratory features of myelofibrosis and limitations of current therapies", Clinical Advances in Hematology and Oncology, 2011, vol. 9, No. 9, pp. 1-3.
Grivennikov, et al., "IL-6 and STAT3 are required for survival of intestinal epithelial cells and the development of colitis-associated cancer", Cancer Cell, 2009, vol. 15, pp. 103-111.
Groneberg, et al., "Animal models of allergic and inflammatory conjunctivitis," Allergy, 2003, vol. 58, pp. 1101-1113.
Guillon, "Tear film photography and contact lens wear", J Br Contact Lens Assoc, 1982, vol. 5, pp. 84-87.
Gura, "Systems for identifying new drugs are often faulty", Science, 1997, vol. 278, No. 5340, pp. 1041-1042.
Guschin, et al, "A major role for the protein tyrosine kinase JAKI in the JAKISTAT signal transduction pathway in response to interleukin-6", Embo J 1995, vol. 14, p. 1421-1429.
Hamze et al., "Synthesis of Various 3-Substituted 1,2,4-Oxadiazole-Containing Chiral 133- and r-Amino Acids from Fmoc-Protected Aspartic Acid," J. Org. Chem., 2003, vol. 68, No. 19, pp. 7316-7321.
Hardwicke, et al., "GSK1070916, a potent Aurora B/C kinase inhibitor with broad antitumor activity in tissue culture cells and human tumor xenograft models", Molecular Cancer Therapeutics 2009, vol. 8, No. 7, pp. 1808-1817.
Harper Collins Publishers, Coilins English Dictionary "in vitro" and "in vivo", p. 852, 2007.
Helal et al., "Stereoselective Synthesis of cis-1,3-Disubstituted Cyclobutyl Kinase Inhibitors," Organic Letters, 2004, vol. 6, No. 11, pp. 1853-1856.
Holly et al., "Lacrimation kinetics in Humans as determined by a novel technique", in Holly FJ (ed): The preocular tear film. Lubbock TX, Lubbock Dry Eye Institute, 1986, pp. 76-88.
Hong, et al., "Total Synthesis of Onnamide A", J. Am. Chem. Soc., 1991, vol. 113, pp. 9693-9694.
Huang, "inhibition of STAT3 activity with AG490 decreases the invasion of human pancreatic cancer ceils in vitro", Cancer Sci. 2006, vol. 97, No. 12, pp. 1417-1423.
Huttel, et al., "Lithium pyrazole compounds". Liebigs Ann. Chem. Bd., 1959, vol. 625, pp. 55-65 (abstract provided).
Iranpoor, et al., "A Rapid and Facile Conversion of Primary Amides and Aldoximes to Nitriles and Ketoximes to Amides with Triphenylphosphine and N-Chlorosuccinimide", G Syn. Commun 2002, vol. 32, pp. 2535-2541.
Ishizaki, et al., "Pharmacological Properties of Y-27632, a Specific Inhibitor of Rho-Associated Kinases", Molecular Pharmacology, 2000, vol. 57, pp. 976-983.
Itagaki, et al,"Expedient Synthesis of Potent Cannabinoid Receptor Agonist (-)-CP55,940", Organic Letters, 2005, vol. 7, No. 19, pp. 4181-4183.
James, et al., "A unique conal JAK2 mutation leading to constitutive signalling causes polycythaemia vera", Nature, 2005, vol. 434, No. 7037, pp. 1144-1148.
Janes, et al., "Effective and selective targeting of leukemia cells using a TORC1/2 kinase inhibitor.", Nature Medicine 2010, vol. 16, No. 2, pp. 205-213.
Jee, et al., "Overview: animal models of osteopenia and osteoporosis", J Musculoskel. Neuron, Interact., 2001, vol. 1, No. 3, pp. 193-207.
Jester, et al., "In vivo biomcroscopy and photography of meibomian glands in a rabbit model of meibomian gland dysfunction", Invest Ophthalmol Vis Sci, 1982, vol. 22, pp. 660-667.
Johnson, et al., "The effect of instiled fluorescein solution volume on the values and repeatability of TBUT measurements", Cornea, 2005, vol. 24, pp. 811-817.
Kaercher. T., "Ocular symptoms and signs in patients with ectodermal dysplasia symdromes", Grafes Arch Clin Exp Ophthalmol, 2004, pp. 495-500.
Kamb, "What's wrong with our cancer models?" Nature Reviews Drug Discovery 2005, vol. 4, pp. 161-165.
Kaushansky, K., "Lineage-Specific Hematopoietic Growth Factors", NEJM 2006, vol. 354, pp. 2034-2045.
Kawamura, et al., "Molecular cloning of L-JAK, a Janus family protein-tyrosine kinase expressed in natural killer cells and activated leukocytes.", Proc Natl Acad Sci USA, 1994, vol. 91, No. 14, pp. 6374-6378.
Kharas, et al., "ABL Oncogenes and Phosphoinositide 3-Kinase: Mechanism of Activation and Downstream Effectors.", Cancer Res., 2005, vol. 65, No. 6, pp. 2047-2053.
Kim, et al., "Zinc-Modified Cyanoborohydride as a Selective Reducing Agent", J. Org. Chem. 1985, vol. 50, pp. 1927-1932.
King-Smith et al., "Three interferometric methods for measuring the thickness of layers of the tear film", Optom Vis Sci, 1999, vol. 76, pp. 19-32.
Kiss, Robert, "Recent developments on JAK2 inhibitors: A patent review", Expert Opinion on Therapeutic Patents, 2010, vol. 20, No. 4, pp. 471-495.
Kojima et al., "A new noninvasive tear stability analysis system for Sie assessment of dry eyes", Invest Ophthalmol Vis Sci, 2004, vol. 45, No. 5, pp. 369-374.
Kola, "Can the pharmaceutical industry reduce attrition rates?" Nature Reviews Drug Discovery 2004, vol. 3, pp. 711-715.
Komuro et al., "Assessment of meibomian gland function by a newly developed laser meibomeles", Adv Exp Med Biol, 2002, vol. 506, pp. 517-520.
Korb et al., "The effect of two novel lubricant eye drops on tear film lipid layer thickness in subjects with dry eye symptoms", Optom Vis Sci, 2005, vol. 82, pp. 594-601.
Korb, et al., "Increase in tear film lipid layer thickness following treatment of meibomian gland dysfunction", Adv Exp Med Biol, 1994, vol. 350, pp. 293-298.
Korolev, et al., "Pd-EDTA as an efficient catalyst for Suzuki-Miyaura reactions in water", Tet. Lett. 2004, vol. 46, pp. 5751-5754.
Kortylewski, et al., "Regulation of the IL-23 and IL-12 balance by Stat3 signaling in the tumor microenvironment", Cancer Cell, 2009, vol. 15, pp. 114-123.
Kruh et al., "The complete coding sequence of arg defines the Abelson subfamily of cytoplasmic tyrosine kinases.", Proc. Natl. Acad. Sci., 1990, vol. 87, pp. 5802-5806.
Kudelacz, et al. "The JAK-3 inhibitor CP-690550 is a potent anti-inflammatory agent in a murine model of pulmonary eosinophilia", European Journal of Pharmacology 2008, vol. 582, pp. 154-161.
Kumar, "Kinase drug discovery approaches in chronic myeloproliferative disorders", Oncogene, 2009, vol. 28, No. 24, pp. 2305-2323.
Kuo, et al., "Pd-EDTA as an efficient catalyst for Suzuki-Miyaura reactions in water", Chem Commun 2007, pp. 301-303.
Kuppens et al., "Basal tear turnover and topical timolol in glaucoma patients and healthy controls by Fluorophotometry", Invest Ophthalmol Vis Sci, 1992, vol. 33, pp. 3442-3448.

(56) References Cited

OTHER PUBLICATIONS

Lai, et al., "Mechanistic Study on the Inactivation of General Acyl-CoA Dehydrogenase by a Metabolite of Hypoglycin A", J. Am. Chem. Soc. 1991, vol. 113, pp. 7388-7397.
Lam, et al, "Tear Cytokine Profiles in Dysfunctional Tear Syndrome", Am J Ophthalmol., 2009, vol. 147, No. 2, pp. 198-205.
Larock, R., "Comprehensive Organic Transformations", Wiley-VCH, 2nd Ed. (1999) pp. 1949-1950, 1958-1959, 1976, and 1983-1985.
Leaf, Health Administrator 2005, vol. XVII, No. 1, pp. 172-183.
Lemp, "Report of National Eye Institute/Industry Workshop on clinical trials in dry eyes", CLAO J, 1995, vol. 21, pp. 221-232.
Lemp, et al., "Corneal desiccation despite normal tear volume", Ann Ophthalmol, 1970, No. 2, pp. 258-261 & 284.
Lemp, et al., "The Definition and Classification of Dry Eye Disease: Report of the Definition and Classification Subcommittee of the International Dry Eye Workshop", The Ocular Surface, 2007, vol. 5, No. 2, pp. 75-92.
Levine, et al., "Activating mutation in the tyrosine kinase JAK2 in polycythemia vera, essential thrombocythemia, and myeloid metaplasia with myelofibrosis", Cancer Cell, 2005, vol 7, pp. 387-397.
Levitzki, "Tyrosine kinases as targets for cancer therapy", Eur. J. Cancer 2002, vol. 38, Suppl. 5, pp. S11-S18.
Levy, et al. "INCB018424 A Selective Janus Kinase ½ Inhibitor" Presentation at the 50th American Society of Hematology Annual Meeting (ASH), Dec. 8, 2008.
Levy, et al., INCB18424 Discussion presentation at the American Society of Hematology, 49th Annual Meeting and Exposition, Atlanta, GA, Abstract #558, Dec. 10, 2007 (25 pages).
Li, et al., "Pim-3, a proto-oncogene with serine/threonine kinase activity, is aberrantly expressed in human pancreatic cancer and phosphorylates Bad-mediated apoptosis in human pancreatic cell lines" Cancer Research 2006, vol. 66, No. 13, pp. 6741-6747.
Lin, "Constitutive Activation of JAK3/STAT3 in Colon Carcinoma Tumors and Cell Lines", Am J Pathol. 2005, vol. 167, No. 4, pp. 969-980.
Lin, et al., "Enantioselecve synthesis of Janus kinase inhibitor INCB016424 via an organocatalytic aza—Michael reaction," Organic Letters, 2009, vol. 11, No. 9, pp. 1999-2002.
Liu, et al., "Combined Inhibition of Janus Kinase ½ for the Treatment of JAK2V617F-Driven Neoplasms: Selective Effects on Mutant Cells and Improvements in Measures of Disease Severity", Clin. Cancer Res. 2009, vol. 15, No. 22, pp. 6891-6900.
Macchi, et al., "Mutations of Jak-3 gene in patients with autosomal severe combined immune deficiency (SCID)", Nature 1995, vol. 377, pp. 65-68.
Madden, et al. Comparative study of two non-invasive tear film stability techniques. Curr Eye Res, 1994, vol. 13, No. 4, pp. 263-269.
Madhusudan et al., "Tyrosine kinase inhibitors in cancer therapy", Clin Biochem., 2004, vol. 37, No. 7, pp. 618-635.
Maffioli, et al., "Mild and Reversible Dehydration of Primary Amides with PdCl2 in Aqueous Acetonitrile", Org. Lett., 2005, vol. 7, No. 23, pp. 5237-5239.
Main, et al., "High throughput synthesis of diverse 2,5-disubstituted indoles using titanium carbenoids bearing boronate functionality", Telrahedron, 2007, vol. 64, No. 5, pp. 991-914.
Mainstone, et al., "Tear meniscus measurement in the diagnosis of dry eye", Curr Eye Res, 1996, vol. 15, pp. 653-661.
Mancini, et al., "RAD 001 (everolimus) prevents mTOR and Akt late re-activation in response to imatinib in chronic myeloid leukemia,", J. Cellular Biochemistry, 2010, vol. 109, No. 2, pp. 320-328.
Manjula, et al. "Rapid Method of Converting Primary Amides to Nitriles and Nitriles to Primary Amides by ZnCl2 using Microwaves under Different Reaction Conditions", Syn. Conmun. 2007, vol. 37, pp. 1545-1550.
Manjula, et al. "The Protein Kinase Complement of the Human Genome", Science, 2002, vol. 298, Iss. 5600, pp. 1912-1916 and 1933-1934.
Manning, et al., "The Protein Kinase Compiement of the Human Genome", Science. 2002, vol. 298, No. 5600, p. 1912-1916 and 1933-1934.
March, Jerry, Advanced Organic Chemistry: Reactions, Mechanisms, and Structure, 3rd ed., John Wiley & Sons:New 46 York, pp. 845-855 (1985).
Marquardt et al., "Modification of tear film break-up time test for increased reliability" in Holly ed. The Preocular Tear Film inHealth, Disease and Contact Lens Wear. Lubbock, Texas: Dry Eye Institute, 1986, pp. 57-63.
Maruyama, et al., "Effect of environmental conditions on tear dynamics in soft contact lens wearers", Invest Ophthalmol Vis Sci, 2004, vol. 45, No. 8, pp. 2563-2568.
Mathers, "Evaporation from the ocular surface", Exp Eye Res, 2004, vol. 78, pp. 389-394.
Mathers, et al., "Assessment of ths tear film with tandem scanning confocal microscopy", Cornea, 1997, vol. 16, pp. 162-168.
Mathers, et al., "Tear film changes associated with normal aging", Cornea, 1996, vol. 15, pp. 229-334.
Mathers, et al., "Tear flow and evaporation in patients with and without dry eye", Ophthalmology, 1996, vol. 103, pp. 664-669.
Mathers, et al., "Video imaging of the meibomian gland", Arch Ophthalmol, 1994, vol. 112, pp. 448-449.
McNamara, et al., "Fluorometry in contact lens research: The next step", Optom Vis Sci, 1998, vol. 75, pp. 316-322.
Mengher, et al., "Non-invasive tear film break-up time: sensitivity and specificity", Acta Ophthalmol (Copenh), 1986, vol. 64, No. 4, pp. 441-444.
Mesa, et al. "INCB018424, A Selective JAK ½ Inhibitor, Significantly Improves the Compromised Nutritional Status and Frank Cachexia in Patients with Myelofibrosis (MF)" Poster #1760 at the American Society of Hematology Annual Meeting (ASH), Dec. 6, 2008 (19 pages).
Mesa, et al., "Emerging drugs for the therapy of primary and post essential thrombocythemia, post polycythemia vera myelofibrosis", Expert Opinion on Emerging Drugs England, 2009, vol. 14, No. 3, pp. 471-479.
Mesa, et al., "Evaluating the serial use of the myelofibrosis symptom assessment form for measuring symptomatic improvement: Performance in 87 myelofibrosis patients on a JAK1 and JAK2 Inhibitor (INCB018424) clinical trial", Cancer, 2011, vol. 117, No. 21, pp. 4869-4877.
Meydan, et al., "Inhibition of acute lymphoblastic leukaemia by a Jak-2 inhibitor", Nature, 1996, vol. 379, No. 6566, pp. 645-648.
Miethchen, "Micelle-activated reactions. I. Micelle-activated iodination and partial dehalogenation of pyrazoles and 1,2,4-triazoles", Journal F. prakt, Chemie, Band 331, Heft 5, S. 799-805 (1989) (1 page abstract also provided)
Milici, A. J., et al., "Cartilage preservation by inhibition of Janus kinase 3 in two rodent models of rheumatoid arthritis", Arthritis Research & Therapy, 2008, vol. 10, pp. R14 (http://arthritis-research.com/content/10/1/R14) (9 pages).
Minegishi, et al. "Human Tyrosine Kinase 2 Deficiency Reveals Its Requisite Roles in Mutiple Cytokine Signals Involved in Innate and Acquired Immunity" Immunity 2006, vol. 25, pp. 745-755.
Minegishi, et al., "Human Tyrosine Kinase 2 Deficiency Reveals Its Requisite Roles in Multiple Cytokine Signals involved in Innate and Acquired Immunity", Immunity 2006, vol. 25, pp. 745-755.
Mishchenko, et al., "Treatment options for hydroxyurea-refractory disease complications in myeloproliferative neoplasms: JAK2 inhibitors, radiotherapy, splenectomy and transjugular intrahepatic portosystemic shunt", Eur J Haematol. 2010, vol. 85, No. 3, pp. 192-199.
Mishima, "Some physiological aspects of the precorneal tear film", Arch Ophthalmol, 1965, vol. 73, pp. 233-241.
Mishima, et al., "Determination of tear volume and tear flow", Invest Ophthalmol, 1966, vol. 5, pp. 264-276.
Mitsunobu, "The Use of Diethyl Axodicarboxylate and Triphenyiphosphine in Synthesis and Transformation of Natural Products." Synthesis 1981, No. 1, pp. 1-28 (1981).
Miyata, et al., "Stereospecific nucleophilic addition reactions to olefins.", J. Org. Chem. 1991, vol. 56, pp. 6556-6564.

(56) References Cited

OTHER PUBLICATIONS

Miyaura et al., "Palladium-Catalyzed Cross-Coupling Reactions of Organoboron Compounds," Chem. Rev., 1995, vol. 95, pp. 2457-2483.
Cho, et al., "Review of the tear break-up time and a closer look at the tear break-up time of Hong Kong Chinese", Optom Vis Sci, 1993, vol. 70, No. 1, pp. 30-38.
Choi Ha-Soon, et al, "Design and synthesis of 7H-pyrrolo[2,3-d]pyrimidines as focal adhesion kinase inhibitors. Part 1", Bioorg. & Med. Chem. Lett., 2006, vol. 16, No. 8, pp. 2173-2176.
Chu-Moyer, et al., "Preparation of the Four Regioisomeric 2-(Methylthio)oxazolopyridines: Useful Syothons for Elaboration to 2-(Amino subsiituted)oxazolopyridines", J. Org. Chem. 1995, vol. 60, No. 17, pp. 5721-5725.
Cilloni, et al., "Emerging drugs for chronic myeloid leukemia", Expert Opinion on Emerging Drugs, 2010, vol. 15, No. 2, pp. 175-184.
Conklyn, M. et al., "The JAK3 inhibitor CP0690550 selectively reduces NK and CD8+ cell numbers in cynomolgus monkey blood following chronic oral dosing", Journal of Leukocyte Biology, 2004, vol. 76, pp. 1248-1255.
Craig, et al., "Tear lipid layer structure and stability following expression of the meibomian glands.", Ophthalmic Physiol Opt, 1995, vol. 15, No. 6, pp. 569-574.
Daniels et al., "Imatinib mesylate inhibits ths profibrogenic activity of TGF-? and prevents bleomycinmediated lung fibrosis," J. Clin. Invest., 2004, vol. 114, No. 9, pp. 1308-1316.
Danjo, et al., "Observation of precorneal tear film in patients with Sjogren's syndrome", Acta Ophthatmol Scand, 1995, vol. 73, pp. 501-505.
De Paiva, et al, "IL-17 disrupts corneal barrier following desiccating stress", Mucosal Immunol. 2009, vol. 2, No. 3, pp. 243-253.
De Vos, et al."JAK2 tyrosine kinase inhibitor tyrphostin AG490 downregulates the mitogen-activated protein kinase (MAPK) and signal transducer and activator of transcription (STAT) pathways and induces apoptosis in myeloma cells.", Br J Haematol, 2000, vol. 109, No. 4, pp. 823-828.
Deng Jun, et al, "Rh-catalyzed asymmetric hydrogenation of gamma-phthalimido-substituted esters: an efficient enantioselective synthesis of beta-aryl-gamma-amino acids", Org. Lett. 2007, vol. 9, No. 23, pp. 4825-4827.
Deuse, et al., "Novel Immunosuppression: R348, a JAK3- and Syk-Inhibitor Attenuates Acute Cardiac Allograft Rejection", Transplantation, 2008, vol. 85, No. 6, pp. 885-892.
Doane, "An instrument for in vivo tear film interferometry", Optom Vis Sci, 1989, vol. 66, pp. 383-388.
Doleschall, et al., "Thermal and Acid Catalysed Degradations of 3-alkylthio-6,7-dihydro[1.2.4]triazino[1,6-c]quinazolin-5-ium-1-olates", Tetrahedron, 1974, vol. 30, pp. 3997-4012.
Dudley, et al. "AVEGF/JAK2/STAT5 axis may partially mediate endothelial cell tolerance to hypoxia", Biochem. J. 2005, vol. 390(Pt 2), pp. 427-436.
Eghtedar, "Phase II Study of the JAK Inhibitor, INCB018424, in Patients with Refractory Leukemias including Post-Myeloproliferative Disorder Acute Myeloid Leukemia", American Society of Hematology (ASH) annual meeting in Orlando, FL (Dec. 6, 2010), Abstract/poster 509.
Einmahl, et al., "Therapeutic applications of viscous end injectable poly(ortho esters)", Adv. Drug. Deliv. Rev. 2001, vol. 53, pp. 45-73.
Eliason, et al., "Staining of the conjunctiva and conjunctival tear film", Br J Ophthalmol, 1990, vol. 74, pp. 519-522.
Expert Scientfic Group "Expert Scientific Group on Phase One Clinical Trials Final Report", Nov. 30, 2006, pp. C1, C35-C38.
Fabrizio, et al., "Ocular inserts for topical delivery", Advanced Drug Delivery Reviews 1998, vol. 16, pp. 95-106.
Farrell, et al., "A classification for dry eyes following comparison of tear thinning time with Schirmer tear test", Acta Ophthalmol (Copenh), 1992, vol. 70, No. 3, pp. 357-360.
Farrell, et al., "A clinical procedure to predict the value of temporary occlusion therapy in keratoconjuncivitis sicca" Ophthal Physiol Opt, 2003, vol. 23, pp. 1-8.
Farris, "Tear osmolarity—a new gold standard?" Adv Exp Med Biol, 1994, vol. 350, pp. 495-503.
Flex, et al., "Somatically acquired JAK1 mutations in adult acute lymphoblastic leukemia", J. Exp Med. 2008, vol. 205, pp. 751-758.
Fonseca, et al., "Interleukin-6 as a key player in systemic inflammation and joint destruction", Autoimmunity Reviews, 2009, vol. 8, pp. 538-542.
Fridman, et al., "Preclinical evaluation of local JAK1 and JAK2 inhibition in cutaneous infammation", Journal of Investigative Dermatology, 2011, vol. 131, No. 9, pp. 1838-1844.
Fridman, J. el al. "Selective JAK inhibition is Efficacious against Multiple Myeloma Cells and Reverses the Protective Effects of Cytokine and Stromal Cell Support" Abstract #0956, presented Sunday, Jun. 15, 2008 at the European Hematology Association, 13th Congress, Jun. 12-15, Copenhagen, Denmark (1 page).
Fridman, Jordan et al. "Discovery and Preclinical Characterization of INCB018424, a Selective JAK2 Inhibitor for the Treatment of Myeloproliferative Disorders" poster presented al the American Society of Hematology, 49th Annual Meeting and Exposition, GA. Abstract #3538, poster #757, Dec. 10, 2007 (1 page).
Fridman, Jordan et al. "Efficacy and Tolerability of Novel JAK Inhibitors in Animal Models of Rheumatoid Arthritis" poster presented at the ACR/ARHP (American College of Rheumatology/Association of Rheumatology Health Professionals) Scientific Meeting 2007, Boston, MA, Nov. 10, 2007, Abstract 1771, poster 285 (1 page).
Fridman, Jordan, et al. "Discovery and Preclinical Development of Selective JAK Inhibitors for the Treatment of Hematological Malignancies" poster presented at European Hematology Association, 12th Congress, Vienna, Austria. Abstract 0324, Jun. 8, 2007 (1 page).
Fridman, Jordan, et al. "Discovery and Preclinical Development of Selective JAK Inhibitors for the Treatment of Myeloproliferative Disorders" poster presented at the 4th International Congress on Myeloproliferative Diseases and Myelodysplastic Syndromes, New York, NY. Nov. 8-10, 2007. Poster 0009 (1 page).
Fujihara, et al., "Evaluation of human conjunctival epithelium by a combination of brush cytology and flow cytometry: an approach to the quantitative technique", Diagn Cytopathol, 1997, vol. 17, pp. 456-460.
Fujii, et al., "Aberrant expression of serine.thereonine kinase Pim-3 in hepatocellular carcinoma development and its role in the proliferation of human hepatoma cell lines" International Journal of Cancer 2005, vol. 114, pp. 209-218.
Fukagawa, et al., "Histological evaluation of brush cytology of rabbit conjunctiva", Nippon Ganka Gakkai Zasshi, 1993, vol. 97, pp. 1173-1178 (contains English abstract within the article).
Gadamasetti et al., "Process Chemistry in the Pharmaceutical Industry," Challenges in an Ever Changing Climate, 2008, vol. 2, pp. 49-63.
Gaertner, "Cyclization of I-Alkyamino-3-halo-2-alkanolst o 1-Alkyl-3-azetidinols," J. Org. Chem., 1967, vol. 32, pp. 2972-2976.
Ghelardi, et al., "A Mucoadhesive Polymer Extracted from Tamarind Seed Improves the Intraocular Penetration and Efficacy of Rufloxacin in Topical Treatment of Experimental Bacterial Keratitis", Antimicrob. Agents Chemother. 2004, vol. 48, pp. 3396-3401
Glasson, et al., "Differences in clinical parameters and tear film of tolerant and intolerant contact lens wearers", Invest Ophthalmol Vis Sci, 2003, vol. 44, pp. 5116-5124.
Glattfeld, "Improvements in the Preparation of DL-Threonic and DL-Erythronic Acids", J. Am. Chem. Soc. 1940, vol. 62, pp. 974-977.
Gobbels, et al., Tear secretion in dry eyes as assessed by objective fluorophotometry, Ger J Ophthalmol, 1992, vol. 1, pp. 350-353.
Golding, et al., "X-ray and scanning eleciron microscopic analysis of the structural composition of tear ferns", Cornea 1994, vol. 13, No. 1, pp. 58-66.
Gomtsyan, et al, "Design, synthesis, and stucture-activity relationship of 6-alkynylpyrimidines as potent adenosine kinase inhibitors", J. Med. Chem. 2002, vol. 45, No. 17, pp. 3639-3648.

(56) References Cited

OTHER PUBLICATIONS

Gooseman, et al., "The intramolecular b-fluorine . . . ammonium interaction in 4- and 8-membered rings", Chem. Commun, 2006, vol. 30, pp. 3190-3192.
Gorre, M.E. et al., "Clinical Resistance to STI-571 Cancer Therapy Caused by BCR-ABL Gene Mutation or Amplification." Science, 2001, vol. 293, p. 876.
Gotlieb, Alice, Presentation at the 2008 American Academy of Dermatology, 66th Annual Meeting, San Antonio, TX. Feb, 1, 2008, symposium-303 (12 pp.).
Goto et al., "Evaluation of the tear film stability after laser in situ keratomileusis using the tear film stability analysis system", Am J Ophthalmol, 2004b, vol. 137, No. 1, pp. 116-120.
Goto, et al. Color mapping of tear lipid layer thickness distribution from the image analysis in DR-1 tear lipid layer . Interferenceimages (ARVO abstract), ARVO 2004.
Goto, et al., "Computer-synthesis of an interference color chart of human tear lipid layer by a colorimetric approach", Invest Ophthalmol Vis Sci, 2003, vol. 44, pp. 4693-4697.
Ahmed et al. "Treatment of Pemphigus Vulgaris with Rituximab and Intravenous Immune Globulin," The New England Journal of Medicine, 2006, 1772-1779.
Anonymous, "Ruxolitinib for Patients with Low or Intermediate-1Risk Myelodysplastic Syndrome (MDS)," ClinicalTrials.gov archive, Aug. 2013 XP002739581. Retieved from the Internet: URL: clinicatrails.gov/archive/NCT01895842/2013_08_19 [retrieved on Apr. 30, 2015], 5 pages.
Arber et al., "The 2016 revision to the World Health Organization classification of myeloid neoplasmas and acute leukemia," Blood, May 2016, 2391-2405.
Bain et al., "Chronic neutrophilic leukaemia," in: Swerdlow et al., eds. WHO Classification of Tumors Haematopoietic Lymphoid Tissues (ed 4th). Lyon: IARC Press. 2098:38-39.
Baxter et al., "Acquired mutation of the tyrosines kinase JAK2 in human myeloproliferative disorders," Lancet, 2005, 365:1054-1061.
Baxter et al., "Reductive Animations of Carbonyl Compounds with Borahydride and Borane Reducing Agents," Organic Reactions, 2002, 1-57.
Beck et al., "Brief Report: Alleviations of Systematic Manifestations of Castleman's Disease by Monoclonal Anti-Interleukin-6 Antibody," N. Engl. J. Med., 1994, 330(9):602-605.
Bennett et al., Proposals for the classificalion of the myelodysplastic syndromes,: British Journal of Haematology, 1982, 51:189-199.
Blom et al., "Optimizing Preparative LC/MS Configurations and Methods for Parallel Synthesis Purification," J. Comb. Chem., 2003, 5:670-683.
Blom et al., "Preparative LC-MS Purfication Improved Compound-Specific Method Optimization," J. Comb. Chem., 2004, 6:874-883.
Blom et al., "Two-Pump at Column-Dilution Configuration for Preparative Liquid Chromatography—Mass Spectrometry," J. Comb. Chem. 2002, 4:295-301.
Bock et al., "Managing drug resistance in cancer: lessons from HIV therapy," Nature, Jul. 2012, 12:494-501.
Bollrath et al., "gp130-Medialed Stat3 Activation in Enterocytes Regulates Cell Survival and Cell Cycle Progression during Colitis-Associated Tumorigenesis," Cancer Cell, 2009, 15:91-102.
Bondoux et al., "Palladium-catalyzed C—C coupling efficient preparation of new 5-thio-B-D-xylopyranosides as oral venous antithrombotic drugs," Tetrahedron Letters, 2009, 50(27):3872-3786.
Brett et al., "Structural chemistry of polycyclic heteroaromatic compound. Part 4. Electronic structures of angular dithienopyridines," J. Chem. Soc., Perkin Trans 2, Jan. 1, 1994, 9:2045.
Brunning et al. "Myelodysplastic syndromes/neoplasms, overview," WHO Classification of Tumours of Haematopoietic and Lymphoid Tissues, 4th Edition, 2008, 88-103.
Brunton et al., "Chemotherapy of Neoplastic Diseases," Goodman & Gillman's: The Pharmacological Basis of Therapeutics. 11th edition, 2008, 853-908.
Cazzola et al. American Society of Hematology (ASH Education Book), 2011(1), 2011, 264-272.
Chari et al. "Complete Remission Achieved with Single Agent CNTO 328, an Anti-IL-6 Monoclonal Antibody, in Relapsed and Refractory Myeloma," Clinical Lymphoma, Myeloma & Leukemia 2013, 13(3):333-337.
Chauhan et al., "A concise review on sustained drug delivery system and its opportunities," International Journal on Pharmtech Research, Mar. 2012, 2:227-238.
Chemical encyclopedia publication "Soviet Encyclopedia," Moscow, 1988, 1:242-243.
Chen et al., "Blockade of interlekeukin-6 signaling augments regulatory T-cell reconstitution and attenuates the severity of graft-versus-host disease," Blood, Jul. 2009, 114(4):891-900.
Chen et al., "Induction of myelodysplasia by myeloid-derived suppresor cells," J. Clin. Invest, Nov. 2013, 123(11):4595-611.
Cheson et al., "Report of an international working group to standardize response criteria for myelodysplastic syndromes," Blood, Dec. 2000, 96(12):3671-4.
Claessens et al., "In vitro proliferation and differentiation of erythroid progenitors from patients with myelodysplastic syndromes: evidence for Fas-dependent apoptosis," Blood, Mar. 2002, 46(12):3143-3150.
Claridge et al., "Discovery of a novel and potent series of thienol[3,2-b]pyridine-based inhibition of C-Met and VEGFR2 tyrosine kinases," Bioorganic & Medicinal Chemistry Letters, 2008, 2793-2798.
Clinical Trial NCT01787487 (487 Trial), dated Feb. 7, 2013, 6 pages.
ClinicalTrials.gov, <http:clinicaltrials.gov/ct2/show/NCT00227591>, downloaded Dec. 6, 2016.
Cottet and Schlosser, "Three Chloro(trifuoromethyl)pyridines as Model Substrates for Regioexhaustive Functionalization," Eur J Org Chem, 2004, 18:3793-3798.
Divkovic et al., "Hapten-protein binding: from theory to practical application in the in vitro prediction of skin sensitization," Contact Dermatitis, 2005, 189-200.
Dorwald, "Side Reactions in Organic Synthesis: A Guide to Successful Synthesis Design," Wiley-VCH, 2005, Chapter 1, 32 pages.
Eghtedar et al., "Phase II Study of the JAK kinase inhibtor ruxolitinib in patients with refractory leukemias, including postmyeloproliferative neoplasm acute myeloid leukemia," Blood, May 2012, 119(20):4614-4618.
Elliott et al., "WHO-defined chronic neutrophilic leukemia: a long-term analysis of 12 cases and a critical review of the literature," Leukemia, 2005, 19:313-317.
Fayad et al., "Interleukin-6 and interleukin-10 levels in chronic lymphocytic leukemia: correlation with phenotypic characteristics and outcome," Blood, Jan. 2001, 97(1):256-263.
Fenaux et al., "A randomized phase 3 study of lenalidomide versus placebo in RBC transfusion-dependent patients with Low-/Intermidiate-1-risk myelodysplastic syndromes with del5q," Blood, Oct. 2011, 118(14):3765-76.
Fenaux et al., "Efficacy of azacitidine compared with that of conventional care regimens in the treatment of higher-risk myelodysplastic syndromes: a randomised, open-label phase III study," Lancet Oncol., Mar. 2009, 10:223-32.
Fiskus et al., "Synergistic Activity of Combinations of JAK2 Kinase Inhibitor with PI3K/mTOR, MEK or PIM Kinase 39 Inhibitor Against Human Myeloproliferative Neoplasm Cells Expressing JAK2V617F" J. American Chem. Soc., 52nd Annual Meeting of the American-Society-of-Hematology (ASH); Orlando, FL, USA; Dec. 4-7, 2010, ACS Publications; vol. 116, No. 21 Nov. 1, 2010 p. 349, XP002667216, ISSN:0002-7863 (1 page).
Fleischman et al., "The CSF3R T6181 mutation causes a lethal neutrophilic neoplasma in mice that is responsive to therapeutic JAK inhibition," Blood, Nov. 2013, 122:3628-3632.
Forbes et al., "Synthesis and evaluation of a series of aryl [e] fused pyrazolo [4,3-c]pyridines with potential anxiolytic activity," J. Medicinal Chem., Jan. 1, 1990, 33(9):2640-2645.
Foucar, "Myelodysplastic/Myelopraliferativee Neoplasms," Am J Olin Pathol, 2009, 132:261-289.

(56) References Cited

OTHER PUBLICATIONS

Fridman et al., "Preclinical evaluation of local JAK1 and JAK2 inhibition in cutaneous inflammation", Journal of investigative Dermatology, Sep. 2011, 13(9):1838-1844.
Gastel et al., "Targeting Innate immunity protein kinase signaling in inflammation," Nat Rev Drug Discov., Jun. 2009, 8(6):480-99.
Gilchrist et al., "5H-2-Pyrindines from 2-Bromocyclopentene-1-carboxaldehyde," Tetrahedron, Jan. 1, 1995, 9119-9126.
Goodman et al., "IL-6 Signaling in Psoriasis Prevents Immune Suppression by Regulatory T Cells," J. Immunol., Sep. 2009, 183:3170-3176.
Goto et al., "Evaluation of the tear film stability after laser in situ keratomileusis using ths tsar film stability analysis system," Am J Ophthalmol, Jan. 2004, 137(1):116-20.
Geenberg, "The Role of Hemopoietic Growth Factors in the Treatment of Myelodysplastic Syndromes," International Journal of Pediatric Hematology/Oncology, 1997, 4(3):231-238.
Geenberg, "The myelodysplastic syndromes" in Hoffman et al, eds. Hematology: Basic Principles and Practice (3rd ed.), Churchill Livingston; 2000:1106-1129.
Greene et al., Greene's Protective Groups in Organic Synthesis, 2007, 4th Edition, 54-55.
Grossman et al., "Interleukin 6 expressed in high levels in psoriatic skin and stimulates proliferation of cultured human keratinocytes," Proc. Natl. Acad., Sci. USA, Aug. 1989, 86:6367-6371.
Gurran et al., "C—C Cross-Coupling Reactions of )6-Alky-2-Haloinosine Derivatives and a One-Pot Cross-Coupling/)6-Deprotection Procedure," Chem Asian J., Aug. 2012, 7(8):1853-1861.
Harris et al., "Alkyl 4-Chlorobenzoyloxycarbanates as Highly Effective Nitrogen Source Reagents for the Bass-Free, Intermolecular Aminolydroxysation Reaction," J. Org. Chem., 2011, 76:358-372.
Harris et al., "World Health Organization classification of neoplastic diseases of the hematopoietic and lymphoid tissues: report of the Clinical Advisory Committee meeting—Airlie House, Virgina, Nov. 1997," J Clin Oncol, 1999, 17:3835-3849.
Heine et al., "The JAK-inhibitor ruxolitinib impairs dendritic cell function in vitro and in vivo," Blood, 2013, 122(7):1192-1202.
Hernandez et al., "Clinical hematological and cytogenetic characteristics of atypical chronic myeloid leukemia," Ann. Oncol., Apr. 2000, 11(4):441-444.
Hickenbottom "Reactions of organic compounds," State Scientific-Technical Publishing Association, Chemical Literature Section, Moscow, 1939, pp. 360-362.
Hyung-Bae et al., "CP-690560, a Janus Kinase Inhibitor Suppresses CD4+ T-Cell-Mediated Acute Gaft-Versus-Host Disease by Inhibiting the Interferon-Y Pathway," Transplantation, 2010, 90(8):825-835.
Jadersten et al., "Long-term outcome of treatment of anemia in MDS with erythropoietin and G-CSF," Blood, Aug. 2005, 106(3):803-11.
Kaddis et al., "Second-Line Treatment for Pancreatic Cancer," Journal of the Pancreas, Jul. 2014, XP055147286, Retrieved from the Internet : URL: http://www.serena.unina.it/index.php/jop/article/viewFile/2691/2737 [retrieved on Oct. 17, 2014].
Kantarjian et al. "Decitabine improves patient outcomes in myelodysplastic syndromes: results of phase III randomized study," Cancer, Apr. 2006, 106(6):1794-803.
Killedar et al. "Early pathogenic events assocaited with Sjogren's syndrome (SjS)-like disease of the NOD mouse using microarray analysis," Lab Invest, Dec. 2006, 86(12):1243-1260.
Kontzias et al. "Jakinibs: a new class of kinase inhibitors in cancer and autoimmune disease." Curr. Opin. Pharm., 2012, 12:464-70.
Kurzock et al., "Serum Interleukin 6 Levels Are Elevated in Lymphoma Patients and Correlate with Survival in Advanced Hodgkin's Disease and with B Symptoms," Cancer Res., May 1993, 52:2118-2122.
Kurzrock et al., "A Phase 1, Open-Label Study of Situximab, an Anti-II-6 Monoclonal Antibody, in Patients with B-cell Non-Hodgkin Lymphoma, Mutiple Myeloma, or Castleman Disease," Clin. Cancer Res., published online May 9, 2013, 39 pages.
Kuster, "Kinase Inhibitors," Methods and Protocols, 2012, 46 pages.
Larson, "Myelodysplasia: when to treat and how," Best PRact Res Clin Haematol 2006, 19(2):293-300.
Lasho et al., "Chronic neutrophilic leukemia with concurrent CSF3R and SETBP1 mutations: single colony clonallity studies, in vitro sensitivity to JAK inhibitors and lack of treatment response to ruxolitnib," Leukemia 2014, 3 pages.
Li et al., "The synthesis and antitumor activity if 5.7-disubstituted pyrazolo [1,5,-a] pyrimidines," Chinese J Med Chem, Feb. 28, 2007, 17(1):18-22.
Lima and Barreiro, "Bioisosterism: a useful strategy for molecular modification and drug design," Curr Med Chem, 2005, 12(1):23-49.
Ling et al., "Knockdowm of STAT3 Expression by RNA Interference Inhibits the Induction of Breast Tumors in Immunocompetent Mice," Cancer Res., Apr. 2005, 65:2532.
List et al., "Efficacy of lenalidomide in myelodysplestic syndromes," N Engl J Med. Feb. 2005, 352(6):549-57.
Libbert et al., "Cytogenic responses in high-risk myelodysplastic syndrome following low-dose treatment with the DNA methylation inhibitor 5-aza-2'-deoxycytidine," Br J Haematol, Aug. 2001, 114(2):349-57.
Libbert et al, "Low-dose decitabine versus best supportive care in elderly patients with intermediate- or high-risk myelodysplastic syndrome (MDS) ineligible for intensive chemotherapy: final results of the randomized phase III study of the European Organization for Research and Treatment of Cancer Leukemia Group and the German MDS Study Group," J Clin Oncol, May 2011, 29(15):1987-96.
Lucet et al., "The structural basis of Janus kinas 2 inhibitor by a potent and specific pan-Janus kinase inhibitor," Blood, 2006, 107(1):176-183.
Mandal, "Cancer Classification," 2014. Available from <http//www.news-medical.net/heaith/CancerClassification.aspx, 6 pages.
Mao et al., "Advances in research tyrosine kinases inhibitor of vascular endothelial growth factorreceptor," Chinese J. New Drugs, Dec. 31, 2008, 17(7):544-550.
Marelli et al., "Tumor targeting via integrin ligands," Frontiers in Oncology, 2013, 1-12.
Mascarenhas et al., "Ruxolitnib: The First DNA Approved Therapy for the Treatment of Myelofibrosis," Clinical Cancer Research, Jun. 2012, 18(11):3008-3014.
Matano et al., "Deletion of the long arm of chromosome 20 in a patient with chronic neutrophilic leukemia: cytogenic findings in chronic neutrophilic leukemia," Am. J. Hematol., Jan. 1997, 54(1):72-5.
Maxson et al., "Oncogenic CSF3R Mutations in Chronic Neutrophilic Leukemia and Atypical CML," N. Engl. J. Med., 2013, 368(19):1781-1790.
Mayo Clinic. Available at: <http://www.mayoclinic.com/health/pancreatic-cancer/DS00357>, 2 pages, retrieved from the Internet Apr. 3, 2013.
Mayo Clinic. Available at: <http://www.mayoclinic.com/health/prostate-cancer-prevention/MC0027>. 3 pages, retrieved from the Internet Apr. 3, 2013.
Mayo Clinic. Available at: <http://www.mayoclinic.com/health/crohns-disease/DS00104/DSECTION=treatments-and-drugs>. 6 pages, retrieved from the Internet May 27, 2013.
Mayo Clinic. Available at: <http://www.mayoclinic.com/health/multiple-sclerosis/DS00188/DSECTION=treatment-and-drugs>, 3 pages, retrieved from the internet May 27, 2013.
Mayo Clinic. Available at: <http://www.mayoclinic.com/health/myasthenia-gravis/DS00375>. 2 pages, retrieved from the Internet May 27, 2013.
Mayo Clinic. Available at: <http://www.mayoclinic.com/health/rheumatoid-arthritis/DS00020/DSECTION=treatment-and-drugs>, 3 pages, retrieved from the Internet Jun. 26, 2013.
Mayo Clinic. Available at: <http://www.mayoclinic.org/diseases-conditions/type-1-diabetes/basics/prevention>. 2014, 19 pages.
McMillan, "The systemic inflammnation-based Glasgow Prognostic Score: a decade of experience in patients with cancer," Cancer Treat Rev, Aug. 2013, 39(5):534-40.

(56) References Cited

OTHER PUBLICATIONS

MD Anderson Cancer Center. "Leukemia Prevention and Screening," 2014, 2 pages.
MD Anderson Cancer Center, "Myeloproliferative Disease Prevention and Screening," 2014, 2 pages.
Meyer et al., "Anti-inflammatory activity and neutrophil reducton mediated by the JAK1/JAK3 inhibitor, CP-690,550, in rat adjuvant-induced arthritis," Journal of Inflammation, 2010, 1-12.
Molldrem et al., "Antithymocyte globulin for patients with myelodysplastic syndrome," Br J Haematol, Dec. 1997, 99(3):699-705.
Mundle et al., "Evidence for Involvement of Tumor Necrosis Factor-alpha tn Apototic Death of Bone Marrow Celis in Myelodysplastic Syndromes," Am J Hematol, 1999, 60:36-47.
Neuner et al., "Increased IL-6 Production by Monocytes and Keratinocytes in Patients with Psoriasis," J. Invest. Dermatol., 1991, 97:27-33.
Nishimoto et al., "Improvement in Castleman's disease by humanized anti-inteleukin-6 receptor antibody therapy," Blood, 2000, 95(1):56-61.
Norman, "Selective JAK1 inhibitor and selective Tyk2 inhibitor patents," Expert Opinion, Informa Healthcare 2012, available at [http://informalhealthcare.com/dol/pdfplus/10.1517/13543776.2012.723693].
Ostojic et al. "Ruxolitinib: a new JAK1/2 inhibitor that offers promising options for treatment of myelofibrosis," Future Oncology, 2011, 7(9):1035-1043.
Panteli et al., "Serum interleukin (IL)-1, IL-2, sIL-2Ra, IL-6 and thrombopoiedn levels in patients with chronic myeloproliferative diseases," British Journal of Haematology, 2005, 130:709-715.
Robin el al., In vivo transillumination biomicroscopy and photography of meibomian gland dysfunction. Ophthalmology, 1985, vol. 92, pp. 1423-1426.
Rodig, et al. "Disruption of the Jak1 gene demonstrates obligatory and nonredundant roles of the Jaks in cytokine-induced biologic responses." Cell, 1998, vol. 93, No. 3, pp. 373-383.
Rolando et al., "Tear mucus crystallization in children with cystic fibrosis", Ophthalmologica, 1988, vol. 197, No. 4, pp. 202-206.
Rolando et al., "Tear mucus ferning test in keratoconjunctivitis sicca", Holly FJ, Lamberts DW, MacKeen DL (eds.): The preocular tear film in health, disease, and contact lens wear,. 1st Intern Tear Film Symposium, Lubbok (Texas, USA), Dry Eye Institute, 1986, pp. 203-210.
Rolando et al., "The effect of hyperosmolarity on tear mucus ferning", Fortschr Ophthalmol, 1986, vol. 83, pp. 644-646.
Rolando, "Tear mucus feming test in normal and keratoconjunctivitis sicca eyes." Chibret Int J Ophthalmol, 1984, vol. 2, No. 4, pp. 32-41.
Rolando, et al., The Ocular Surface and Tear Film and Their Dysfuntion in Dry Eye Disease, Survey of Ophthalmology, 2001, vol. 45, Suppl. 2, pp. S203-S210.
Roudebush, et al., "Pharmacologic manipulation of a four day marine delayed type hyper sensitivity model", Agents Actions, 1993, vol. 38, No. 1-2, pp. 116-121.
Rausvoal, et al. "Janus kinase 3 inhibition with CP-690,550 prevents allograft vasculopathy", Transpl Int., 2006, vol. 19, No. 12, pp. 1014-1021.
Saemann, et al., "Prevention of CD40-triggered dendritic cell maturation and induction of T-cell hyporeactivily by targeting of Janus kinase 3", Am J Transplant, 2003, vol. 3, No. 11, pp. 1341-1349.
Saettone, et al. "Ocular inserts for topical delivery," Advanced Drug Delivery Reviews, 1995, vol. 16, pp. 95-106.
Samana et al., "Janus kinass 2: a critical target in chronic myelogenous leukemia", Cancer Res. 2006, vol. 66, No. 13, pp. 6468-6472.
Sawadam et al., "Increased Lipophilicity and Subsequent Cell Partitioning Decrease Passive Transcellular Diffusion of Novel, Highly Lipophilic Antioxidents", The Journal of Pharmacology and Experimental Therapeutics, 1999, vol. 3, No. 288, pp. 1317-1326, p. 1321, compound 26.
Schindler, et al., "Hormones and Signaling: Cytokines and STAT Signaling", Adv Pharmacol. 2000; 47:113-74.
Schrader, et al., "Animal Models of Dry Eye," Developmental Opthalmology, Karger 2008, vol. 41, pp. 298-312.
Scott, et al., "Jaks, STATs, Cytokines, and Sepsis", Clin Diagn Lab Immunol, 2002, vol. 9, No. 6, pp. 1153-1159.
Seefeld, et al, "Discovery of 5-pyrrolopyridinyl-2-thiophenecarboxamides as potent AKT kinase", Bioorganic & Medicinal Chemistry Letters. 2009, vol. 19, No. 8, pp. 2244-2248.
Seela, et al., "Synthesis of Pyrrolo[2,3-d]pyrimidine 2',r-Dideoxyribenucleosides Related to 2',3-Dideoxyadenosine and 2',3"-Dideoxgtuanosine and Inhibitory Activity of 5"-Triphosphates on HIV-1 Reverse Transcriptase", Helvetica Chimica, Acta, 1991, vol. 74, No. 3, pp. 554-564.
Seki, "STAT3 and MAPK in human lung cancer tissues and suppression of oncogenic growth by JAB and dominant negative STAT3", Int J Oncol. 2004, vol. 24, No. 4, pp. 931-934.
Seto, et al., "Enhanced Th2 cell-mediated allergic inflammation in Tyk2-deficient mice", J Immunol. 2003, vol. 170, No. 2, pp. 1077-1083.
Shah, et al., "Multiple BCR-ABL kinase domain mutations confer polygonal resistance to the tyrosine kinase inhibitor imatinib (STI571)in chronic phase and blast crisis chronic myeloid leukemia." Cancer Cell, 2002, vol. 2, pp. 117-125.
Shi, et al., "The pharmacokinetics, pharmacodynamics, and safety of orally dosed INCB018424 phosphate in healthy volunteers", Journal of Clinical Pharmacology, 2011, vol. 51, No. 12, pp. 1644-1654.
Shimazaki et al., "Meibomian gland dysfunction in patients with Sjogren syndrome", Ophthalmology, 1998, vol. 105, No. 8, pp. 1485-1488.
Smith et al., "Basic pathogenic mechanisms operating in experimental model acute anterior uveitis," Immunology and Cell Biology, 1998, vol. 76, pp. 497-512.
Smolen, et al, "Effect of interleukin-6 receptor inhibition with tocilizumab in patients with rheumatoid arthritis (OPTION study): a double-blind, placebo-controlled, randomized trial", Lancet 2008, vol. 371, pp. 987, 2008.
Sriram, et al., "Induction of gp130-related Cytokines and Activation of JAK2/STAT3 Pathway in Astrocytes Precedes Up-regulation of Glial Fibrillary Acidic Protein in the 1-Methyl-4-phenyl-1,2,3,6-tetrahydropyridine Model of Neurodengeneralion", J. Biol. Chem., 2004, vol. 279, No. 19, p. 19936-19947.
Staerk, et al., "JAK1 and Tyk2 activation by the homologous polycythemia vera JAK2 V617F mutation: cross-talk with IGF1 receptor", J Biol Chem., 2005, vol. 280, pp. 41893-41899.
Stirewalt et al., "Predictors of relapse and overall survival in Philadelphia chromosome-positive acute lymphoblastic leukemia after transplantation", Biol Blood Marrow Transplant, 2003 , vol. 9, No. 3, pp. 206-212.
STN Search conducted Aug. 30, 2010 (17 pages).
STN Search conducted Jun. 24, 2011 (24 pages).
STN Search conducted Nov. 5, 2010 (5 pages).
STN Search conducted Nov. 9, 2010 (43 pages).
STN Search, Nov. 12, 2009 (180 pages).
STN Search, Oct. 20, 2009 (601 pages).
STN Search, Sep. 20, 2009 (864 pages).
Sullivan, et al., "4th International Conference on the Lacrimal Gland, Tear Film & Ocular Surface and Dry Eye Syndromes, Nov. 20, 2004" (2 pages).
Takahashi, et al., "Solvent-Free Reaction Using Pmospwonium Salts: Chlorination of Hydroxyheteroaromatics and dehydration of Primary Amides", Heterocycles 2006, vol. 68, pp. 1973-1979.
Takano, et al., "Inflammatory cells in brush cytology samples correlate with the severity of corneal lesions in atopic keratoconjunctivitis", Br J Ophthalmol, 2004, vol. 88, pp. 1504-1505.
Takemoto, et al., "Proliferation of adult T cell leukemka/lymphoma cells is associated with the constitutive activation of JAK/STAT proteins." Proc Natl Acad Sci USA, 1997, vol. 94, No. 25, pp. 13897-13902.
Tan, et al, "Racemization processes at a quaternary carbon center in the context of the asymmetric Michael reaction", Tetrahedron Lett., 2061, vol. 42, No. 30, pp. 5021-5023.

(56) References Cited

OTHER PUBLICATIONS

Tang, et al., "Knowledge-based design of 7-azaindoles as selective B-Raf inhibitors", Bioorganic & Medicinal Chemistry Letters 2008, vol. 18, No. 16, pp. 4610-4614.
Tasian, et al., "Understanding the biology of CRLF2-overexpressing acute lymphoblastic leukemia", Critical Reviews in Oncogenesis, 2011, vol. 16, No. 1-2, pp. 13-24.
Tefferi, et al. "Serious adverse events during ruxolitinib treatment discontinuation in patients with myelofibrosis", Mayo Cinic Proceedings, 2011, vol. 86, No. 12, pp. 1188-1191.
Tefferi, et al., The Clinical Phenotype of Myelofibrosis Encompasses a Chronic Inflammatory State that is Favorably Altered by INCB018424, A Selective Inhibitor of JAK1/2"Poster #2804 at the American Society of Hematology Annual Meeting (ASH), Dec. 7, 2008, (18 pages).
Tefferi, "Primary myelofibrosis: 2012 update on diagnosis, risk stratification, and management", American Journal of Hematology, 2011, vol. 86, No. 12, pp. 1017-1026.
Thompson, et al., "Photochemical Preparation of a Pyricone Containing Tetracycle: A Jak Protein Kinase Inhibitor", Bioorganic & Medicinal Chemistry Letters, 12 (2002) 1219-1223.
Tiffany, "Refractive index of meibomian and other lipids", Curr Eye Res, 1986, vol. 5, pp. 887-889.
Tiffany, et al., Meniscametry using ths Tearscope-plus (ARVO abstract). Invest Ophthalmol Vis Sci, 2001, vol. 42, No. S37 (1 page).
Toyonaga, "Blockade of constitutively activated Janus kinase/signal transducer and activator of transcription-3 pathway inhibits growth of human pancreatic cancer", Cancer Lett. 2003, vol. 201, No. 1, pp. 107-116.
Tsubota et al. "Conjunctival brush cytology", Acta Cytol, 1990, vol. 34, No. 2, pp. 233-235.
Tsubota et al., "Detection by brush cytology of mast cells and eosinophils in allergic and vernal conjunctivitis"; Cornea, 1991, vol. 10, No. 6, pp. 525-531.
Tsubota, et al., "Brush cytology for the evaluation of dry-eye", Nippon Ganka Gakkai Zasshi, 1990a, vol. 94, pp. 224-300n Japanese with English abstract).
U.S. National Institute of Health, "Open Label Ruxolitinib (INCB018424) in Patients with Myelofibrosis and Post Polycythemia Vera/Essential Thrombocythemis Myelofibrosis," Dec. 19, 2014, available ate www.clinicaltrials.gov, 4 pages.
U.S. National Institute of Health, "Study of Ruxolitinib," Dec. 3, 2008, available at www.clinicaltrials.gov, 11 pages.
Ueda et al., "1,2-Benzisoxazol-3-y1 Diphenyl Phosphate: A New, Reactive Activating Agent for the Synthesis of Amides, Esters, and Peptides via Condensation", J. Org. Chem. 1985, vol. 50, pp. 760-763.
Van Best et al., "Measurement of basal tear turnover using a standardized protocol", Graefe's Arch Clin Exp Ophthalmol, 1995, vol. 233, pp. 1-7
Van Bijsterveld, "Diagnostic tests in the sicca syndrome", Arch Ophthalmol, 1969, vol. 82, pp. 10-14.
Vannucchi, et al., "Inhibitorsof PI3K/Akt and/or mTOR Inhibit the Growth of Cells of Myeloproliferative Neoplasms and Synergize with JAK2 Inhibitor and Interferon", Blood, 2011, vol. 118, No. 21, pp. 1638-1639, XP008150742ASH Annual Meeting Abstract 3835 American Society of Hematology.
Vannucchi, et al., "RAD001, An Inhibitor of mTOR, Shows Clinical Activity in a Phase I/II Study in Patients with Primary Myelofibrosis (PMF) and Post Polycythemia Vera/Essential Thrombocythemia Myelofibrosis (PPV/PET MF)", Blood, ASH Annual Meeting Abstracts 307, 2009, vol. 114, No. 22 (2 pages).
Vannucchi, et al., "The mTOR Inhibitor, RAD001, Inhibits the Growth of Cells From Patients with Myeloproliferative Neoplasms", Blood: ASH Annual Meeting Absracts, 51st Annual Meeting of the American Society of Hematology, 2009, vol. 114, No. 22 (2 pages).

Vasilevsky, et al., "Ethyl Vinyl Ether—an Agent for Protection of the Pyrazole NH-Fragment. A Convenient Method for the Preparation of N-Unsubstituted 6-Alkynypyrazoles", Heterocycles, 2003, vol. 60, No. 4, pp. 879-886.
Verma, et al., "Jak family of kinases in cancer", Cancer and Metastasis Reviews, 2003, vol. 22, No. 4, pp. 423-434.
Verstovsek, "Therapeutic Potential of JAK2 inhibitors", Hematology Am Soc Hematol Educ Program, 2009, pp. 636-642.
Verstovsek, et al. "The JAK Inhibitor INCB018424 Demonstrates Durable and Marked Clinical Responses in Primary Myelofibrosis (PMF) and Post-Polycythemia/Essential Thrombocythemia Myelofibrosis (Post-PV/ET-MF)" Poster #1762 at the American Society of Hematology Annual Meeting (ASH), Dec. 6, 2008 (19 pages)
Verstovsek, et al. "The selective Janus kinase (JAK) inhibitor, INCB018424, shows efficacy in phase I/II trial in patients with primary myelofibrosis (PMF) and post polycythemia vera/essential thrombocythemia myelofibrosis (Post-PV/ET MF)" Abstract #0444, presented Saturday, Jun. 14, 2008 at the European Hematology Association, 13th Congress, Jun. 12-15, Copenhagen, Denmark (2 pages).
Verstovsek, et al. INCB18424, an Oral, Selective JAK2 Inhibitor, Shows Significant Clinical Activity in a Phase I/II Study in Patient with Primary Myelofibrosis (PMF) and Post Polycythemia Vera/Essential Thrombocythemia Myelofibrosis (Post-PV/ET MF), presentation at the American Society of Hematology 49th Annual Meeting and Exposition, Dec. 10, 2007 (16 pages).
Verstovsek, et al., "Characterization of JAKS V617F Allele Burden in Advanced Myelofibrosis (MF) Patients: No Change in V617F:WT JAK2 Ratio in Patients with High Allele Burdens despite Profound Clinical Improvement Following Treatment with the JAKL inhibitor, INCB018424," 50th ASH Annual Meeting and Exposition, Abstract No. 2802 (2008).
Vitali, et al. "The European Community Study Group on diagnostic criteria for Sjogren's syndrome. Sensitivity and specificity of tests for ocular and oral involvement in Sjogren's syndome." Ann Rheum Dis, 1994, vol. 53, No. 10, pp. 637-647.
Wagh, et al., "Polymers used in ocular dosage fosm and drug delivery systems", Asian J. Pharm., pp. 12-17.
Webster's New World Medical Dictionary, Sjogren's syndrome, 2003, Wiley Publishing, printed fro http://www.credoreference.com/entry/webstermed/sjogren_s_syndrome, 2 pages.
Weiss, et al., "Evaluation of a Series of Naphthamides as Potent, Orally Active Vascular Endothelial Growth Factor Receptor-2 Tyrosine Kinase Inhibitors", J. Med Chem., 2008, vol. 61, pp. 1668-1680.
Welch et al., "An approach to a more standardized method of evaluating tear film break-up time", Invest Ophthalmol Vis Sci, 2003; 24851B324 (abstract only—2 pages).
White et al., "Human basic tear fluid osmolality. I. Importance of sample collection strategy", Acta Ophthalmol (Copenh), 1993, vol. 71, No. 4, pp. 524-529.
Williams et al. "Carbohydrate Chemistry: Recent Advances", Chem. Rev. 1981, vol. 81, pp. 589-636.
Williams, et al. "Initial Efficacy of INCB018424, a selecive Janus Kinasel& 2 (JAK1&2) inhibitor in Rheumatoid Arthritis (RA)," European League Against Rheumatism (EULAR) meeting presentation and abstract (Jun. 11-14, 2006, Paris, France), Annals Rheum Dis 67SII:62, 2008.
Wolf, et al., "Burger's Medicinal Chemistry and Drug Discovery", 5th Ed. Part I, pp. 975-977 (1995).
Wu et al., One-Pot Two-Step Microwave-Assisted Reaction in Construction 4,5-Disubstituted Pyrazolopyrimidines Organic Letters, 2003, vol. 5, No. 20, pp. 3587-3590.
Xiaoyang et al., "Knockdown of STAT3 Expression by RNA interference Inhibits the Induction of Breast Tumors in Immunocompetent Mice", Cancer Res 2005, vol. 65, p. 2532.
Yamaoka et al., "Janus kinase (JAK) inhibitors in rheumatoid arthritis", Current Rheumatology Reviews, 2011, vol. 7, No. 4, pp. 306-312.
Yang et al., "Constitutive NF-kB activation confers interleukin 6 (IL6) independence and resistance to dexamethasone and Janus

(56) References Cited

OTHER PUBLICATIONS kinase inhibitor INCB018424 in murine plasmacytoma cells", Journal of Biological Chemistry, 2011, vol. 286, No. 32, p. 27988-27997.
Yao, et al. "Glucocorticoid-Induced Bone Loss in Mice Can Be Reversed by the Actions of Parathyroid Hormone and Risedronate on Different Pathways for Bone Formation and Mineralization", Arthritis and Rheumatism, 2008, vol. 58, pp. 3485-3497.
Yao, et al., "Glucocorticoid Excess in Mice Results in Early Activation of Osteoclastogenesis and Adipogenesis and Prolonged Suppression of Osteogenesis", Arthritis and Rheumatism, 2008, vol. 58, No. 6, pp. 1674-1686.
Yokoi et al., "A newly developed video-meibography system featuring a newly designed probe", Jpn J Ophthalmol, 2007, vol. 51, pp. 53-56.
Yokoi et al., "Assessment of meibomian gland function in dry eye using meibometry", Arch Ophthalmol, 1999, vol. 117, pp. 723-729.
Yokoi et al., "Correlation of tear lipid layer interference patterns with the diagnosis and severity of dry eye", Am J Ophthalmol, 1996, vol. 122, pp. 818-824.
Yokoi et al., "Non-invasive methods of assessing the tear film", Exp Eye Res, 2004, vol. 78, pp. 399-407.
Yu, et al., "Constitutive activation of the Janus kinase-STAT pathway in T lymphoma overexpressing the Lck protein tyrosine kinase", J Immunol. 1997, vol. 159, No. 11, pp. 5206-5210.
Zheng, et al., "Discovery of INCB108201PF-4178903, a potent, selective, and orally bioavailable dual CCR2 and CCR5 antagonist", Bioorganic & Medicinal Chemistry Letters 2011, vol. 21, pp. 1442-1445.
Zoppellaro, et al., "A Multifunctional High-Spin Biradical Pyrazolyibipyridine-bisnitronyinitroxide", Org. Lett. 2004, Vol. , No. 26, pp. 4929-4932.
Zou, et al., "Signaling Pathways Activated by Oncogenic Forms of Abl Tyrosine Kinase," Journal of Biological Chemistry, 1997, vol. 274, No. 26, p. 18141-18144.
International Preliminary Report on Patentability corresponding to International Patent Application No. PCT/US2008/066658, dated Dec. 17, 2009, 7 pgs.
International Preliminary Report on Patentability corresponding to International Patent Application No. PCT/US2008/066662, dated Dec. 17, 2009, 7 pgs.
International Preliminary Report on Patentability corresponding to International Patent Application No. PCT/US2009/036635, dated Sep. 14, 2010, 6 pgs.
International Preliminary Report on Patentability corresponding to International Patent Application No. PCT/US2009/059203, dated Apr. 5, 2011, 6 pgs.
International Preliminary Report on Patentability corresponding to International Patent Application No. PCT/US2010/021003, dated Jul. 19, 2011, 11 pgs.
International Preliminary Report on Patentability corresponding to International Patent Application No. PCT/US2010/035728, dated Nov. 22, 2011, 8 pgs.
International Preliminary Report on Patentability corresponding to International Patent Application No. PCT/US2010/035783, dated Nov. 22, 2011, 5 pgs.
International Preliminary Report on Patentability corresponding to International Patent Application No. PCT/US2010/047252, dated Mar. 5, 2012, 7 pgs.
International Preliminary Report on Patentability corresponding to International Patent Application No. PCT/US2010/052011, dated Apr. 11, 2012, 4 pgs.
International Preliminary Report on Patentability corresponding to International Patent Application No. PCT/US2011/025433, dated Aug. 21, 2012, 7 pgs
International Preliminary Report on Patentability corresponding to International Patent Application No. PCT/US2011/027665, dated Sep. 11, 2012, 7 pgs.
International Search Report corresponding to International Patent Application No. PCT/US2008/066658, dated Dec. 23, 2008, 4 pgs.
International Search Report corresponding to International Patent Application No. PCT/US2010/021003, dated Aug. 16, 2010, 8 pgs.
International Search Report corresponding to International Patent Application No. PCT/US2010/035728, dated Jul. 8, 2010, 3 pgs.
International Search Report corresponding to International Patent Application No. PCT/US2010/035763, dated Aug. 23, 2010, 4 pgs.
International Search Report corresponding to International Patent Application No. PCT/US2010/047252, dated Nov. 17, 2010, 4 pgs.
International Search Report corresponding to International Patent Application No. PCT/US2010/052011, dated Nov. 30, 2010, 3 pgs.
International Search Report with Written Opinion corresponding to International Patent Application No. PCT/US2005/046207, dated May 15, 2007, 6 pgs.
International Search Report with Written Opinion corresponding to International Patent Application No. PCT/US2006/047369, dated Apr. 24, 2007, 16 pgs.
International Search Report with Written Opinion corresponding to International Patent Application No. PCT/US2008/066662, dated Dec. 23, 2008, 11 pgs.
International Search Report with Written Opinion corresponding to International Patent Application No. PCT/US2008/083319, dated Mar. 13, 2009, 29 pgs.
International Search Report with Written Opinion corresponding to International Patent Application No. PCT/US2009/036635, dated Jun. 3, 2009, 14 pgs.
International Search Report with Written Opinion corresponding to International Patent Application No. PCT/US2009/059203, dated Feb. 9, 2010, 10 pgs.
International Search Report with Written Opinion corresponding to International Patent Application No. PCT/US2011/025433, dated Jul. 20, 2011, 12 pgs.
International Search Report with Written Opinion corresponding to International Patent Application No. PCT/US2011/027665, dated Jun. 27, 2011, 14 pgs.
International Search Report with Written Opinion corresponding to International Patent Application No. PCT/US2011/037291, dated Apr. 19, 2012, 11 pgs.
International Search Report with Written Opinion corresponding to International Patent Application No. PCT/US2011/061351, dated Feb. 17, 2012, 12 pgs.
International Search Report with Written Opinion corresponding to International Patent Application No. PCT/US2011/061374, dated Mar. 27, 2012, 10 pgs.
International Search Report with Written Opinion corresponding to International Patent Application No. PCT/US2012/025581, dated Apr. 26, 2011, 16 pgs.
Notice of Allowance corresponding to U.S. Appl. No. 11/313,394, dated Oct. 11, 2007, 6 pgs.
Notice of Hearing and Preliminary Report for European Patent Application No. 1966202, dated Mar. 18, 2013, 7 pgs.
Office Action corresponding to Canadian Patent Application No. 2,632,466, dated May 8, 2012, 3 pgs.
Office Action corresponding to Chilean Patent Application No. 3496-2006, dated Jul. 5, 2010, 4 pgs.—English tranlation.
Office Action corresponding to Chinese Patent Application No. 200680052750.7, dated Sep. 3, 2010, 8 pgs.
Office Action corresponding to Eurasian Patent Office, prepared Feb. 5, 2010.
Office Action corresponding to European Patent Application No. 06839328.9, dated Jan. 22, 2009, 5 pages.
Office Action corresponding to European Patent Application No. 06839328.9, dated Oct. 21, 2010.
Office Action corresponding to European Patent Application No. 08770791.5, dated Nov. 6, 2009.
Office Action corresponding to Japanese Patent Application No. 2008-545733, dated Oct. 11, 2011, 5 pgs.
Office Action corresponding to Mexico Patent Application No. MX/a/2008/007635, dated Jun. 15, 2010, 1 pg.
Office Action corresponding to Mexico Patent Application No. MX/a/2008/007635, dated Nov. 13, 2009, 4 pgs.
Office Action corresponding to New Zealand Application No. 569015, dated Feb. 24, 2010, 2 pgs.

(56) References Cited

OTHER PUBLICATIONS

Office Action corresponding to Pakistan Patent Application No. 211/2009, dated Jan. 18, 2010, 1 pg.
Office Action corresponding to Singapore Application No. 2008-04386-1, dated Aug. 24, 2010.
Office Action corresponding to Singapore Patent Application No. 2012043428, dated Sep. 26, 2014, 25 pgs.
Office Action corresponding to U.S. Appl. No. 11/115,702, dated Aug. 22, 2007, 9 pgs.
Office Action corresponding to U.S. Appl. No. 11/115,702, dated Feb. 7, 2008, 5 pgs.
Office Action corresponding to U.S. Appl. No. 11/313,394, dated Apr. 20, 2007, 16 pgs.
Office Action corresponding to U.S. Appl. No. 11/524,641, dated Dec. 3, 2007, 13 pgs.
Office Action corresponding to U.S. Appl. No. 12/137,892, dated Feb. 25, 2009, 13 pgs.
Office Action corresponding to U.S. Appl. No. 12/137,892, dated Nov. 30, 2009, 9 pgs.
Office Action corresponding to Vietnamese Patent Application No. 1-2011-03188, dated Mar. 8, 2012, 10 pgs.—English translation only.
Opposition (Actavis) to European Patent Publication No. 2173752, mailed Jan. 20, 2015, 20 pgs.
Opposition (Generics) to European Patent Publication No. EP2173752, mailed Jan. 20, 2015, 18 pgs.
Opposition to Costa Rica Patent Application No. translation from Foreign Associate Dated Jun. 13, 2012, 6 pages.
Opposition to European Patent Publication No. 1966202, filed on Jun. 21, 2012, 30 pgs.
Opposition to India Patent Application No. 2365/KOLNP/2008, dated Nov. 12, 2012, 37 pgs.
Opposition, Ecuador Patent Office, mailed Nov. 18, 2008 1 page letter from Foreign Associate enclosing the translation (5 pages) of the Opposition.
Response and Amendment corresponding to U.S. Appl. No. 11/313,394, filed Jul. 17, 2007, 39 pgs.
Response and Amendment corresponding to U.S. Appl. No. 12/137,892, dated Aug. 25, 2009, 34 pgs.

SALTS OF THE JANUS KINASE INHIBITOR (R)-3-(4-(7H-PYRROLO[2,3-D]PYRIMIDIN-4-YL)-1H-PYRAZOL-1-YL)-3-CYCLOPENTYLPROPANENITRILE

CROSS-REFERENCE TO RELATED APPLICATIONS

This application is a continuation of U.S. application Ser. No. 16/003,210, filed on Jun. 8, 2018, which is a continuation of U.S. application Ser. No. 15/164,518 filed on May 25, 2016, now issued as U.S. Pat. No. 10,016,429, which is a continuation of U.S. application Ser. No. 14/270,915 filed on May 6, 2014, now issued as U.S. Pat. No. 9,376,439, which is a continuation of U.S. application Ser. No. 14/097,588, filed on Dec. 5, 2013, now issued as U.S. Pat. No. 8,722,693, which is a continuation of U.S. application Ser. No. 12/137,892, filed Jun. 12, 2008, which claims the benefit of U.S. Ser. No. 60/943,705, filed Jun. 13, 2007, the disclosure of each of which is incorporated herein by reference in their entireties.

FIELD OF THE INVENTION

The present invention provides salt forms of (R)-3-(4-(7H-pyrrolo[2,3-d]pyrimidin-4-yl)-1H-pyrazol-1-yl)-3-cyclopentylpropanenitrile that are useful in the modulation of Janus kinase activity and are useful in the treatment of diseases related to activity of Janus kinases including, for example, immune-related diseases, skin disorders, myeloid proliferative disorders, cancer, and other diseases.

BACKGROUND OF THE INVENTION

Protein kinases (PKs) are a group of enzymes that regulate diverse, important biological processes including cell growth, survival and differentiation, organ formation and morphogenesis, neovascularization, tissue repair and regeneration, among others. Protein kinases exert their physiological functions through catalyzing the phosphorylation of proteins (or substrates) and thereby modulating the cellular activities of the substrates in various biological contexts. In addition to the functions in normal tissues/organs, many protein kinases also play more specialized roles in a host of human diseases including cancer. A subset of protein kinases (also referred to as oncogenic protein kinases), when dysregulated, can cause tumor formation and growth, and further contribute to tumor maintenance and progression (Blume-Jensen P et al, Nature 2001, 411(6835):355-365). Thus far, oncogenic protein kinases represent one of the largest and most attractive groups of protein targets for cancer intervention and drug development.

The Janus Kinase (JAK) family plays a role in the cytokine-dependent regulation of proliferation and function of cells involved in immune response. Currently, there are four known mammalian JAK family members: JAK1 (also known as Janus kinase-1), JAK2 (also known as Janus kinase-2), JAK3 (also known as Janus kinase, leukocyte; JAKL; L-JAK and Janus kinase-3) and TYK2 (also known as protein-tyrosine kinase 2). The JAK proteins range in size from 120 to 140 kDa and comprise seven conserved JAK homology (JH) domains; one of these is a functional catalytic kinase domain, and another is a pseudokinase domain potentially serving a regulatory function and/or serving as a docking site for STATs (Scott, Godshall et al. 2002, supra).

Blocking signal transduction at the level of the JAK kinases holds promise for developing treatments for human cancers. Inhibition of the JAK kinases is also envisioned to have therapeutic benefits in patients suffering from skin immune disorders such as psoriasis, and skin sensitization. Accordingly, inhibitors of Janus kinases or related kinases are widely sought and several publications report effective classes of compounds. For example, certain JAK inhibitors, including (R)-3-(4-(7H-pyrrolo[2,3-d]pyrimidin-4-yl)-1H-pyrazol-1-yl)-3-cyclopentylpropanenitrile depicted below, are reported in U.S. Ser. No. 11/637,545, filed Dec. 12, 2006.

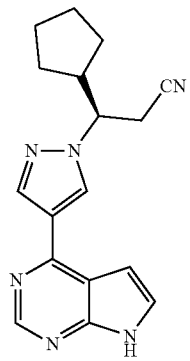 [SMILES: N#CC[C@H](C1CCCC1)n1cc(-c2ncnc3[nH]ccc23)cn1]

Thus, new or improved forms of existing Janus kinase inhibitors are continually needed for developing new, improved, and more effective pharmaceutical formulations for the treatment of cancer and other diseases. The salt forms and methods described herein are directed toward these needs and other ends.

SUMMARY OF THE INVENTION

The present invention provides, inter alia, salts selected from:
(R)-3-(4-(7H-pyrrolo[2,3-d]pyrimidin-4-yl)-1H-pyrazol-1-yl)-3-cyclopentylpropanenitrile maleic acid salt;
(R)-3-(4-(7H-pyrrolo[2,3-d]pyrimidin-4-yl)-1H-pyrazol-1-yl)-3-cyclopentylpropanenitrile sulfuric acid salt; and
(R)-3-(4-(7H-pyrrolo[2,3-d]pyrimidin-4-yl)-1H-pyrazol-1-yl)-3-cyclopentylpropanenitrile phosphoric acid salt.

The present invention further provides methods of preparing a salt of the invention comprising combining (R)-3-(4-(7H-pyrrolo[2,3-d]pyrimidin-4-yl)-1H-pyrazol-1-yl)-3-cyclopentylpropanenitrile with maleic acid, sulfuric acid, or phorphoric acid.

The present invention further provides compositions comprising a salt form of the invention and at least one pharmaceutically acceptable carrier.

The present invention further provides methods of modulating an activity of JAK comprising contacting JAK with a salt of the invention.

The present invention further provides methods of treating a disease in a patient, wherein the disease is associated with JAK activity, comprising administering to the patient a therapeutically effective amount of a salt of the invention.

The present invention further provides methods of treating cancer, skin disorders, or inflammation in a patient, comprising administering to the patient a therapeutically effective amount of a salt of the invention.

The present invention further provides the salts of the invention for use in methods of treating the human or animal body by therapy.

The present invention further provides the salts of the invention for use in treating cancer, skin disorders, or inflammation.

The present invention further provides use of the salts of the invention for the preparation of a medicament for use in the treatment of any of the diseases or disorders recited herein.

DETAILED DESCRIPTION

The present invention provides, inter alia, salts of the JAK inhibitor (R)-3-(4-(7H-pyrrolo[2,3-d]pyrimidin-4-yl)-1H-pyrazol-1-yl)-3-cyclopentylpropanenitrile selected from the maleic acid salt, sulfuric acid salt, and phosphoric acid salt. These salts modulate the activity of one or more JAKs and are useful, for example, in the treatment of diseases associated with JAK expression or activity.

The salts of the invention have numerous advantageous properties over the free base form and other salt forms. In particular, these salts were highly crystalline which would facilitate the preparation of pharmaceutical formulations and improve general handling, manipulation, and storage of the active ingredient. The salts of the invention also have superior aqueous solubility, rate of dissolution, chemical stability (with a longer shelf life), compatibility with excipients, and reproducibility compared with the free base form.

In some embodiments, the salts of the invention are substantially isolated. By "substantially isolated" is meant that the salt is at least partially or substantially separated from the environment in which it was formed or detected. Partial separation can include, for example, a composition enriched in the salt of the invention. Substantial separation can include compositions containing at least about 50%, at least about 60%, at least about 70%, at least about 80%, at least about 90%, at least about 95%, at least about 97%, or at least about 99% by weight of the salt.

Salts of the invention also include all isotopes of atoms occurring in the salts. Isotopes include those atoms having the same atomic number but different mass numbers. For example, isotopes of hydrogen include tritium and deuterium.

Salts of the invention can be prepared using known techniques. Conventionally, a salt form is prepared by combining in solution the free base compound and an acid containing the anion of the salt form desired, and then isolating the solid salt product from the reaction solution (e.g., by crystallization, precipiatation, evaporation, etc.). Other salt-forming techniques can be employed.

Methods of Use

Salts of the invention can modulate activity of one or more Janus kinases (JAKs). The term "modulate" is meant to refer to an ability to increase or decrease the activity of one or more members of the JAK family of kinases. Accordingly, compounds of the invention can be used in methods of modulating a JAK by contacting the JAK with any one or more of the compounds or compositions described herein. In some embodiments, salts of the present invention can act as inhibitors of one or more JAKs. In some embodiments, compounds of the present invention can act to stimulate the activity of one or more JAKs. In further embodiments, the compounds of the invention can be used to modulate activity of a JAK in an individual in need of modulation of the receptor by administering a modulating amount of a salt of the invention.

JAKs to which the present salts bind and/or modulate include any member of the JAK family. In some embodiments, the JAK is JAK1, JAK2, JAK3 or TYK2. In some embodiments, the JAK is JAK1 or JAK2. In some embodiments, the JAK is JAK2. In some embodiments, the JAK is JAK3.

The salts of the invention can be selective. By "selective" is meant that the compound binds to or inhibits a JAK with greater affinity or potency, respectively, compared to at least one other JAK. In some embodiments, the compounds of the invention are selective inhibitors of JAK1 or JAK2 over JAK3 and/or TYK2. In some embodiments, the salts of the invention are selective inhibitors of JAK2 (e.g., over JAK1, JAK3 and TYK2). Without wishing to be bound by theory, because inhibitors of JAK3 can lead to immunosuppressive effects, a compound which is selective for JAK2 over JAK3 and which is useful in the treatment of cancer (such as multiple myeloma, for example) can offer the additional advantage of having fewer immunosuppressive side effects. Selectivity can be at least about 5-fold, 10-fold, at least about 20-fold, at least about 50-fold, at least about 100-fold, at least about 200-fold, at least about 500-fold or at least about 1000-fold. Selectivity can be measured by methods routine in the art. In some embodiments, selectivity can be tested at the Km of each enzyme. In some embodiments, selectivity of salts of the invention for JAK2 over JAK3 can be determined by the cellular ATP concentration.

Another aspect of the present invention pertains to methods of treating a JAK-associated disease or disorder in an individual (e.g., patient) by administering to the individual in need of such treatment a therapeutically effective amount or dose of a salt of the present invention or a pharmaceutical composition thereof. A JAK-associated disease can include any disease, disorder or condition that is directly or indirectly linked to expression or activity of the JAK, including overexpression and/or abnormal activity levels. A JAK-associated disease can also include any disease, disorder or condition that can be prevented, ameliorated, or cured by modulating JAK activity.

Examples of JAK-associated diseases include diseases involving the immune system including, for example, organ transplant rejection (e.g., allograft rejection and graft versus host disease).

Further examples of JAK-associated diseases include autoimmune diseases such as multiple sclerosis, rheumatoid arthritis, juvenile arthritis, type I diabetes, lupus, psoriasis, inflammatory bowel disease, ulcerative colitis, Crohn's disease, myasthenia gravis, immunoglobulin nephropathies, autoimmune thyroid disorders, and the like. In some embodiments, the autoimmune disease is an autoimmune bullous skin disorder such as pemphigus vulgaris (PV) or bullous pemphigoid (BP).

Further examples of JAK-associated diseases include allergic conditions such as asthma, food allergies, atopic dermatitis and rhinitis. Further examples of JAK-associated diseases include viral diseases such as Epstein Barr Virus (EBV), Hepatitis B, Hepatitis C, HIV, HTLV 1, Varicella-Zoster Virus (VZV) and Human Papilloma Virus (HPV).

Further examples of JAK-associated diseases or conditions include skin disorders such as psoriasis (for example, psoriasis vulgaris), atopic dermatitis, skin rash, skin irritation, skin sensitization (e.g., contact dermatitis or allergic contact dermatitis). For example, certain substances including some pharmaceuticals when topically applied can cause skin sensitization. In some embodiments, co-administration or sequential administration of at least one JAK inhibitor of the invention together with the agent causing unwanted sensitization can be helpful in treating such unwanted sensitization or dermatitis. In some embodiments, the skin disorder is treated by topical administration of at least one JAK inhibitor of the invention.

In further embodiments, the JAK-associated disease is cancer including those characterized by solid tumors (e.g., prostate cancer, renal cancer, hepatic cancer, pancreatic cancer, gastric cancer, breast cancer, lung cancer, cancers of the head and neck, thyroid cancer, glioblastoma, Kaposi's sarcoma, Castleman's disease, melanoma etc.), hematological cancers (e.g., lymphoma, leukemia such as acute lymphoblastic leukemia, acute myelogenous leukemia (AML), or multiple myeloma), and skin cancer such as cutaneous T-cell lymphoma (CTCL) and cutaneous B-cell lymphoma. Example cutaneous T-cell lymphomas include Sezary syndrome and mycosis fungoides.

JAK-associated diseases can further include those characterized by expression of a mutant JAK2 such as those having at least one mutation in the pseudo-kinase domain (e.g., JAK2V617F).

JAK-associated diseases can further include myeloproliferative disorders (MPDs) such as polycythemia vera (PV), essential thrombocythemia (ET), myeloid metaplasia with myelofibrosis (MMM), chronic myelogenous leukemia (CML), chronic myelomonocytic leukemia (CMML), hypereosinophilic syndrome (HES), systemic mast cell disease (SMCD), and the like.

Further JAK-associated diseases include inflammation and inflammatory diseases. Example inflammatory diseases include inflammatory diseases of the eye (e.g., iritis, uveitis, scleritis, conjunctivitis, or related disease), inflammatory diseases of the respiratory tract (e.g., the upper respiratory tract including the nose and sinuses such as rhinitis or sinusitis or the lower respiratory tract including bronchitis, chronic obstructive pulmonary disease, and the like), inflammatory myopathy such as myocarditis, and other inflammatory diseases. Other inflammatory diseases treatable by the compounds of the invention include systemic inflammatory response syndrome (SIRS) and septic shock.

The JAK inhibitors described herein can further be used to treat ischemia reperfusion injuries or a disease or condition related to an inflammatory ischemic event such as stroke or cardiac arrest. The JAK inhibitors described herein can further be used to treat anorexia, cachexia, or fatigue such as that resulting from or associated with cancer. The JAK inhibitors described herein can further be used to treat restenosis, sclerodermitis, or fibrosis. The JAK inhibitors described herein can further be used to treat conditions associated with hypoxia or astrogliosis such as, for example, diabetic retinopathy, cancer, or neurodegeneration. See, e.g., Dudley, A. C. et al. *Biochem. J.* 2005, 390(Pt 2):427-36 and Sriram, K. et al. *J. Biol. Chem.* 2004, 279(19):19936-47. Epub 2004 Mar. 2.

The JAK inhibitors described herein can further be used to treat gout and increased prostate size due to, e.g., benign prostatic hypertrophy or benign prostatic hyperplasia.

As used herein, the term "contacting" refers to the bringing together of indicated moieties in an in vitro system or an in vivo system. For example, "contacting" a JAK with a salt of the invention includes the administration of a salt of the present invention to an individual or patient, such as a human, having a JAK, as well as, for example, introducing a salt of the invention into a sample containing a cellular or purified preparation containing the JAK.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active salt or pharmaceutical agent that elicits the biological or medicinal response that is being sought in a tissue, system, animal, individual or human by a researcher, veterinarian, medical doctor or other clinician.

As used herein, the term "treating" or "treatment" refers to one or more of (1) preventing the disease; for example, preventing a disease, condition or disorder in an individual who may be predisposed to the disease, condition or disorder but does not yet experience or display the pathology or symptomatology of the disease; (2) inhibiting the disease; for example, inhibiting a disease, condition or disorder in an individual who is experiencing or displaying the pathology or symptomatology of the disease, condition or disorder; and (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

Combination Therapies

One or more additional pharmaceutical agents such as, for example, chemotherapeutics, anti-inflammatory agents, steroids, immunosuppressants, as well as Bcr-Abl, Flt-3, RAF and FAK kinase inhibitors such as, for example, those described in WO 2006/056399, or other agents can be used in combination with the salts of the present invention for treatment of JAK-associated diseases, disorders or conditions. The one or more additional pharmaceutical agents can be administered to a patient simultaneously or sequentially.

Example chemotherapeutics include proteosome inhibitors (e.g., bortezomib), thalidomide, revlimid, and DNA-damaging agents such as melphalan, doxorubicin, cyclophosphamide, vincristine, etoposide, carmustine, and the like.

Example steroids include coriticosteroids such as dexamethasone or prednisone.

Example Bcr-Abl inhibitors include the compounds, and pharmaceutically acceptable salts thereof, of the genera and species disclosed in U.S. Pat. No. 5,521,184, WO 04/005281, EP2005/009967, EP2005/010408, and U.S. Ser. No. 60/578,491.

Example suitable Flt-3 inhibitors include compounds, and their pharmaceutically acceptable salts, as disclosed in WO 03/037347, WO 03/099771, and WO 04/046120.

Example suitable RAF inhibitors include compounds, and their pharmaceutically acceptable salts, as disclosed in WO 00/09495 and WO 05/028444.

Example suitable FAK inhibitors include compounds, and their pharmaceutically acceptable salts, as disclosed in WO 04/080980, WO 04/056786, WO 03/024967, WO 01/064655, WO 00/053595, and WO 01/014402.

In some embodiments, the salt forms of the invention can be used in combination with other kinase inhibitors such as imatinib, particularly for the treatment of patients resistant to imatinib or other kinases.

In some embodiments, one or more salt forms of the invention can be used in combination with a chemotherapeutic in the treatment of cancer, such as multiple myeloma, and may improve the treatment response as compared to the response to the chemotherapeutic agent alone, without exacerbation of its toxic effects. Examples of additional pharmaceutical agents used in the treatment of multiple myeloma, for example, can include, without limitation, melphalan, melphalan plus prednisone [MP], doxorubicin, dexamethasone, and Velcade (bortezomib). Further additional agents used in the treatment of multiple myeloma include Bcr-Abl, Flt-3, RAF and FAK kinase inhibitors. Additive or synergistic effects are desirable outcomes of combining a JAK inhibitor of the present invention with an additional agent. Furthermore, resistance of multiple myeloma cells to agents such as dexamethasone may be reversible upon treatment with a JAK inhibitor of the present invention. The agents can be combined with the present compounds in a single or continuous dosage form, or the agents can be administered simultaneously or sequentially as separate dosage forms.

In some embodiments, a corticosteroid such as dexamethasone is administered to a patient in combination with at least one JAK inhibitor where the dexamethasone is administered intermittently as opposed to continuously.

In some further embodiments, combinations of one or more JAK inhibitors of the invention with other therapeutic agents can be administered to a patient prior to, during, and/or after a bone marrow transplant or stem cell transplant.

Pharmaceutical Formulations and Dosage Forms

When employed as pharmaceuticals, the salts of the invention can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal, intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

This invention also includes pharmaceutical compositions which contain, as the active ingredient, one or more of the compounds of the invention above in combination with one or more pharmaceutically acceptable carriers (excipients). In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

The compounds of the invention may be milled using known milling procedures such as wet milling to obtain a particle size appropriate for tablet formation and for other formulation types. Finely divided (nanoparticulate) preparations of the compounds of the invention can be prepared by processes known in the art, for example see International Patent Application No. WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 to about 1000 mg (1 g), more usually about 100 to about 500 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, about 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of salt or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the salts of the present invention can vary according to, for example, the particular use for which the treatment is made, the manner of administration of the compound, the health and condition of the patient, and the judgment of the prescribing physician. The proportion or concentration of a salt of the invention in a pharmaceutical composition can vary depending upon a number of factors including dosage, chemical characteristics (e.g., hydrophobicity), and the route of administration. For example, the salts of the invention can be provided in an aqueous physiological buffer solution containing about 0.1 to about 10% w/v of the compound for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compositions of the invention can further include one or more additional pharmaceutical agents such as a chemotherapeutic, steroid, anti-inflammatory compound, or immunosuppressant, examples of which are listed hereinabove.

Labeled Compounds and Assay Methods

Another aspect of the present invention relates to labeled salts of the invention (radio-labeled, fluorescent-labeled, etc.) that would be useful not only in imaging techniques but also in assays, both in vitro and in vivo, for localizing and quantitating JAK in tissue samples, including human, and for identifying JAK ligands by inhibition binding of a labeled compound. Accordingly, the present invention includes JAK assays that contain such labeled compounds.

The present invention further includes isotopically-labeled salts of the invention. An "isotopically" or "radio-labeled" compound is a salt of the invention where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^{2}H$ (also written as D for deuterium), $^{3}H$ (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$ and $^{131}I$. The radionuclide that is incorporated in the instant radio-labeled compounds will depend on the specific application of that radio-labeled compound. For example, for in vitro metalloprotease labeling and competition assays, compounds that incorporate $^{3}H$, $^{14}C$, $^{82}Br$, $^{125}I$, $^{131}I$, $^{35}S$ or will generally be most useful. For radio-imaging applications $^{11}C$, $^{18}F$, $^{125}I$, $^{123}I$, $^{124}I$, $^{131}I$, $^{75}Br$, $^{76}Br$ or $^{77}Br$ will generally be most useful.

It is understood that a "radio-labeled" or "labeled compound" is a salt that has incorporated at least one radionuclide. In some embodiments the radionuclide is selected from the group consisting of $^{3}H$, $^{14}C$, $^{125}I$, $^{35}S$ and $^{82}Br$.

The present invention can further include synthetic methods for incorporating radio-isotopes into compounds of the invention. Synthetic methods for incorporating radio-isotopes into organic compounds are well known in the art, and a person of ordinary skill in the art will readily recognize the methods applicable for the compounds of invention.

A labeled salt of the invention can be used in a screening assay to identify/evaluate compounds. For example, a newly synthesized or identified compound (i.e., test compound) which is labeled can be evaluated for its ability to bind a JAK by monitoring its concentration variation when contacting with the JAK, through tracking of the labeling. For example, a test compound (labeled) can be evaluated for its ability to reduce binding of another compound which is known to bind to a JAK (i.e., standard compound). Accordingly, the ability of a test compound to compete with the standard compound for binding to the JAK directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

Kits

The present invention also includes pharmaceutical kits useful, for example, in the treatment or prevention of JAK-associated diseases or disorders, such as cancer, inflammation, or skin disorders, which include one or more containers containing a pharmaceutical composition comprising a therapeutically effective amount of a salt of the invention. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

EXAMPLES

Example 1: Preparation of (R)-3-(4-(7H-pyrrolo[2,3-d]pyrimidin-4-yl)-1H-pyrazol-1-yl)-3-cyclopentyl-propanenitrile Maleic Acid Salt To a test tube was added (R)-3-(4-(7H-pyrrolo[2,3-d]pyrimidin-4-yl)-1H-pyrazol-1-yl)-3-cyclopentylpropanenitrile (153.7 mg, 0.5 mmol) and maleic acid (61.7 mg) followed by isopropyl alcohol (IPA) (4 mL). The resulting mixture was heated to clear, cooled to room temperature, and then stirred for another 2.5 hours. The precipitate was collected by filtration and the cake was washed with 0.8 mL of cold IPA. The cake was dried under vacuum to constant weight to provide the final salt product (173 mg).

The maleic acid salt was shown to be a 1:1 salt by $H^1$ NMR and crystallinity was confirmed by X-ray powder diffraction (XRPD). Differential scanning calorimetry (DSC) gave a sharp melting peak at about 175.96° C. (onset at 175.67° C.). The product showed only slight weight loss up to 150° C. by thermogravimetric analysis (TGA).

Example 2: Preparation of (R)-3-(4-(7H-pyrrolo[2,3-d]pyrimidin-4-yl)-1H-pyrazol-1-yl)-3-cyclopentyl-propanenitrile Phosphoric Acid Salt To a test tube was added (R)-3-(4-(7H-pyrrolo[2,3-d]pyrimidin-4-yl)-1H-pyrazol-1-yl)-3-cyclopentylpropanenitrile (153.5 mg) and phosphoric acid (56.6 mg) followed by isopropyl alcohol (IPA) (5.75 mL). The resulting mixture was heated to clear, cooled to room temperature, and then stirred for another 2 hours. The precipitate was collected by filtration and the cake was washed with 0.6 mL of cold IPA. The cake was dried under vacuum to constant weight to provide the final salt product (171.7 mg).

The phosphroic acid salt was shown to be a 1:1 salt by $^1$H NMR and crystallinity was confirmed by X-ray powder diffraction (XRPD). Differential scanning calorimetry (DSC) gave a sharp melting peak at about 198.66° C. The product showed little weight loss up to 200° C. by TGA.

Example 3: Preparation of (R)-3-(4-(7H-pyrrolo[2,3-d]pyrimidin-4-yl)-1H-pyrazol-1-yl)-3-cyclopentyl-propanenitrile Sulfuric Acid Salt To a test tube was added (R)-3-(4-(7H-pyrrolo[2,3-d]pyrimidin-4-yl)-1H-pyrazol-1-yl)-3-cyclopentylpropanenitrile (153.0 mg) and sulfuric acid (56.1 mg) followed by acetonitrile (7.0 mL). The resulting mixture was heated to clear, cooled to room temperature, and then stirred for another 2 hours. The precipitate was collected by filtration and the cake was washed with 0.8 mL of cold acetonitrile. The cake was dried under vacuum to constant weight to provide the final salt product (180 mg).

The sulfuric acid salt was shown to be a 1:1 salt by $^1$H NMR and crystallinity was confirmed by X-ray powder diffraction (XRPD). Differential scanning calorimetry (DSC) gave a sharp melting peak at about 186.78° C. The product showed little weight loss up to 175° C. by TGA.

Example A

In Vitro JAK Kinase Assay

Inhibitory activity of test compounds on JAK targets can be tested according to the following in vitro assay described in Park et al., *Analytical Biochemistry* 1999, 269, 94-104. The catalytic domains of human JAK1 (a.a. 837-1142), Jak2 (a.a. 828-1132) and Jak3 (a.a. 781-1124) with an N-terminal His tag are expressed using baculovirus in insect cells and purified. The catalytic activity of JAK1, JAK2 or JAK3 is assayed by measuring the phosphorylation of a biotinylated peptide. The phosphorylated peptide was detected by homogenous time resolved fluorescence (HTRF). $IC_{50S}$ of compounds are measured for each kinase in the reactions that contain the enzyme, ATP and 500 nM peptide in 50 mM Tris (pH 7.8) buffer with 100 mM NaCl, 5 mM DTT, and 0.1 mg/mL (0.01%) BSA. The ATP concentration in the reactions is 90 µM for Jak1, 30 µM for Jak2 and 3 µM for Jak3. Reactions are carried out at room temperature for 1 hr and then stopped with 20 µL 45 mM EDTA, 300 nM SA-APC, 6 nM Eu-Py20 in assay buffer (Perkin Elmer, Boston, Mass.). Binding to the Europium labeled antibody takes place for 40 minutes and HTRF signal is measured on a Fusion plate reader (Perkin Elmer, Boston, Mass.). Both the phosphoric acid salt of the invention, and the corresponding free base compound, were found to have $IC_{50}$ values of less than 50 nM for each of JAK1, JAK2, and JAK3.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

What is claimed is:

1. A pharmaceutical composition comprising a compound that is (R)-3-(4-(7H-pyrrolo[2,3-d]pyrimidin-4-yl)-1H-pyrazol-1-yl)-3-cyclopentylpropanenitrile phosphoric acid salt and one or more pharmaceutically acceptable excipients; wherein the composition is suitable for providing sustained release of the compound.

2. The composition of claim 1, wherein the composition is a unit dosage form.

3. The composition of claim 2, wherein the unit dosage form is a tablet.

4. The composition of claim 2, wherein the unit dosage form is a capsule.

5. The composition of claim 1, wherein the unit dosage form further comprises an enteric layer.

6. The composition of claim 2, wherein the unit dosage form comprises from about 5 to about 1000 mg of the compound.

7. The composition of claim 1, wherein said one or more excipients comprise lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, or methyl cellulose.

8. The composition of claim 1, wherein said one or more excipients comprise microcrystalline cellulose.

9. The composition of claim 8, wherein said one or more excipients comprise lactose.

10. The composition of claim 9, wherein the unit dosage form is a tablet.

11. The composition of claim 1, wherein said one or more excipients comprise lactose.

12. The composition of claim 1, wherein (R)-3-(4-(7H-pyrrolo[2,3-d]pyrimidin-4-yl)-1H-pyrazol-1-yl)-3-cyclopentylpropanenitrile phosphoric acid salt is a crystalline salt.

13. The composition of claim 12, wherein said crystalline salt is a 1:1 (R)-3-(4-(7H-pyrrolo[2,3-d]pyrimidin-4-yl)-1H-pyrazol-1-yl)-3-cyclopentylpropanenitrile:phosphoric acid salt.

14. The composition of claim 13, wherein the unit dosage form is a tablet.

15. The composition of claim 1, wherein the composition suitable for providing sustained release of the compound is administered orally.

16. The composition of claim 1, wherein the composition suitable for providing sustained release of the compound is administered topically.

* * * * *